United States Patent
Dime et al.

(10) Patent No.: US 7,033,765 B1
(45) Date of Patent: Apr. 25, 2006

(54) SITE-SPECIFIC DRUG DELIVERY

(75) Inventors: David S. Dime, Toronto (CA); Peter Backx, Richmond Hill (CA); Klaus Kimmeldirk, Vincent, OH (US)

(73) Assignee: Toronto Research Chemicals, Inc., North York (CA)

( * ) Notice: Subject to any disclaimer, the term of this patent is extended or adjusted under 35 U.S.C. 154(b) by 0 days.

(21) Appl. No.: 09/367,794

(22) PCT Filed: Feb. 19, 1998

(86) PCT No.: PCT/CA98/00133

§ 371 (c)(1),
(2), (4) Date: Jan. 6, 2000

(87) PCT Pub. No.: WO98/36777

PCT Pub. Date: Aug. 27, 1998

Related U.S. Application Data

(60) Provisional application No. 60/042,911, filed on Feb. 20, 1997, and provisional application No. 60/066,635, filed on Nov. 11, 1997.

(51) Int. Cl.
*G01N 33/53* (2006.01)
*G01N 33/566* (2006.01)
*A61K 47/48* (2006.01)

(52) U.S. Cl. .................. 435/7.1; 436/501; 514/707; 530/350; 536/115; 536/54; 536/53; 536/18.7

(58) Field of Classification Search .......... 435/7.1; 436/501; 514/707; 536/115, 54, 53, 18.7; 530/350
See application file for complete search history.

(56) References Cited

U.S. PATENT DOCUMENTS

| 4,386,026 A | 5/1983 | Ponpipom et al. |
| 5,989,827 A | 11/1999 | Fesik et al. ................. 435/7.1 |

FOREIGN PATENT DOCUMENTS

| EP | 0 398 305 B1 | 11/1990 |
| EP | 0 398 305 A2 | 11/1990 |
| EP | 0 512 844 B1 | 11/1992 |
| EP | 0 512 844 A1 | 11/1992 |
| WO | WO 95/10302 | 4/1995 |
| WO | WO 97/23494 | 7/1997 |
| WO | WO 98 00171 A | 1/1998 |

OTHER PUBLICATIONS

L.D. Small, "Synthesis and Preliminary Antimicrobial Screening of Two Thiosulfonates," *Journal of Pharmaceutical Sciences*, 65 (No. 11): 1692–1694 (1976).

Foong et al., "Development of a Novel Thiol Reagent for Probing Ion Channel Structure: Studies in a Model System," *Biochemistry*, 36:1343–1348 (1997).

*Primary Examiner*—Jon Weber
*Assistant Examiner*—Chih-Min Kam
(74) *Attorney, Agent, or Firm*—Townsend and Townsend and Crew LLP

(57) ABSTRACT

Compounds and methods which are useful for the site-specific delivery and localization of drugs are provided. The compounds can be represented by the formula: A-L-D wherein A is an anchoring moiety; L is a linking group; and D is a drug.

12 Claims, 13 Drawing Sheets

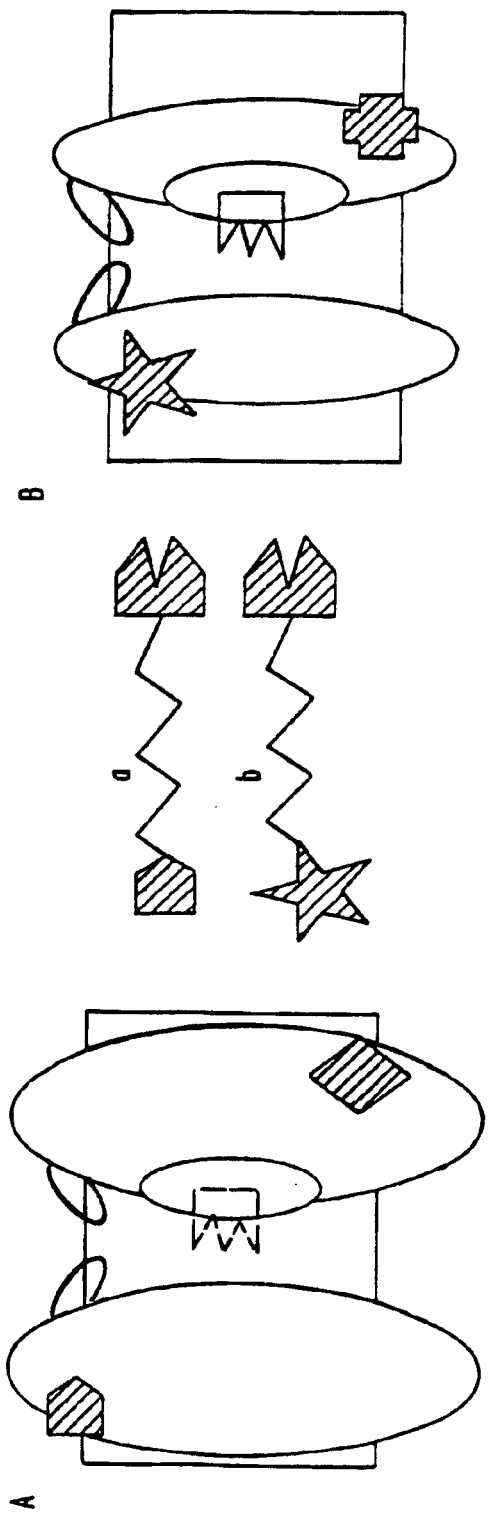
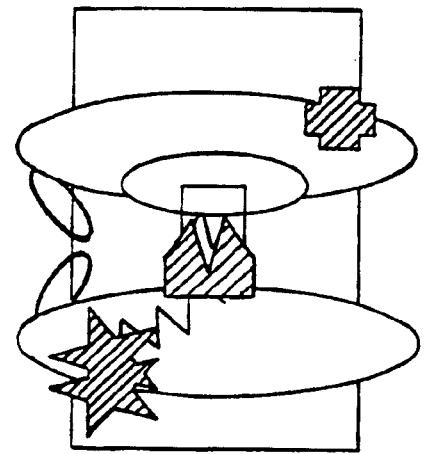
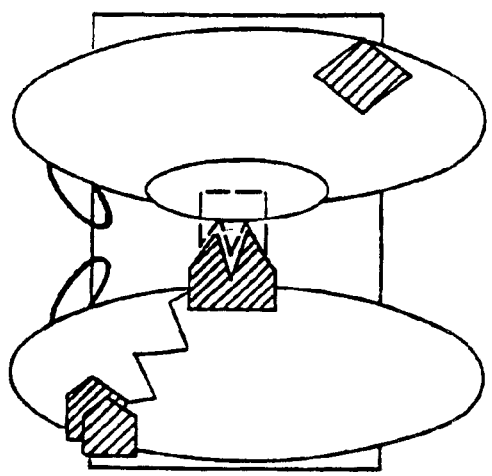
FIG. 1A.
FIG. 1B.

COMPOUND

C2

C5

C10

C5°

C8°

C11°

C14°

T2

L2

L5

L11°

SITE-SPECIFIC DRUG DELIVERY

CROSS-REFERENCE TO RELATED APPLICATIONS

This application is a 371 of application PCT/CA98/00133, filed Feb. 19, 1998, and claims priority to U.S. provisional application Ser. No. 60/042,911, filed on Feb. 20, 1997, and U.S. provisional application Ser. No. 60/066,635, filed on Nov. 11, 1997, both of which are herein incorporated by reference.

FEDERALLY SPONSORED RESEARCH AND DEVELOPMENT

Not applicable.

FIELD OF THE INVENTION

The present invention relates to new methods of drug delivery using modified therapeutic agents. In particular, it relates to the preparation of targeted agents in which a drug has an attached targeting anchor and methods of delivering the modified drug to a predetermined site.

BACKGROUND OF THE INVENTION

Various structural motifs among homologous proteins are conserved. This represents an evolutionary consequence of preserving effective structures necessary for desired protein functions (Creighton, T. E., PROTEINS: STRUCTURE AND MOLECULAR PROPERTIES, W.H. Freeman and Co., New York, pp 201–269 (1993); and Branden, C. & Tooze, J., INTRODUCTION TO PROTEIN STRUCTURE, Garland Publishing Inc., New York, pp 11–77 (1991)). Consequently, there are common peptide structures in similar or ancestrally-related proteins in different tissues and species (e.g., membranous $Ca^{2+}$ channel proteins are found in heart, skeletal muscle, nerve, pituitary glands, β-cells of the pancreas and other tissues). See, Hille, B., IONIC CHANNELS IN EXCITABLE MEMBRANES, Sunderland, M.A., Ed., pp 261–389 (1992).

The ion channel proteins in various tissues are encoded by separate genes and have distinct amino acid sequences. Yet the tertiary structure and functional properties of these proteins are very similar or nearly identical. As a result of the common functional properties of ion channel proteins, the domains (or regions) which confer the essential functional properties to ion channel proteins are very highly, and usually absolutely, conserved. As a result, drugs which modulate ion channel proteins are inherently incapable of being directed specifically to specific ion channel proteins in one tissue without affecting other tissues.

Similarly, other homologous classes of proteins exist (e.g., voltage-gated $Na^+$ and $K^+$ channel proteins, lactate dehydrogenase, etc.) and the use of agents developed to modulate the proteins and thus to treat specific diseases often causes undesired side-effects by interacting with the homologous proteins. For example, fast-acting class 1b antiarrhythmics which modify cardiac $Na^+$ channel proteins, are not widely used to treat ventricular arrhythmias because of neurological toxicity which is a consequence of effects of the drugs on nerve $Na^+$ channel proteins (see, Bean, B. P., et al., *J. Gen. Physiol.* 81:613 (1983) and DeLuca, A., et al., *Naunym-Schmiedeberg's Arch. Pharmacol.* 344:596 (1991)). In another example, $Ca^{2+}$ channel protein blockers which are designed as antihypertension agents often cause undesirable side-effects in the brain, cardiac muscle and skeletal muscle. These side-effects are associated with actions of the blockers. In fact, most classes of therapeutic agents are inherently non-specific and invariably modulate homologous proteins.

The specific targeting or anchoring of drugs to a receptor site would be extremely advantageous, particularly if the drug is toxic. Drugs linked to antibodies, in the form of immunoconjugates, have been used to assist in targeted drug delivery (see, B. A. Froesh, et al., *Cancer Immunol. Immunother.* 42:55 (1996); D. Willner, et al., *Bioconjugate Chem.* 4:521 (1993)). These strategies have limitations as many cellular sites cannot be targeted with immunoconjugates. Moreover, immunoconjugates are typically delivered by injection, thus limiting their widespread use.

What is needed are new compounds and methods of site-specific delivery of pharmaceutical agents. The new compounds would provide alternatives to immunoconjugates by having targeting or anchoring moieties which are not antibody-based. The present invention provides such compounds and methods of delivery.

SUMMARY OF THE INVENTION

The present invention provides compounds and methods which are useful for tissue- or cell-specific delivery and localization of drugs. The compounds can be represented by the formula:

A-L-D wherein A is an anchoring moiety; L is a linking group; and D is a drug. In preferred embodiments, the anchoring moiety is a functional group capable of covalent attachment to a target site. Particularly preferred are those anchoring moieties having a sulfhydryl-reactive group (e.g., alkanethiosulfonate esters, dithiopyridyl groups, maleimide, cystine, etc. Other particularly preferred embodiments are those in which the anchoring moiety is a reactive functional moiety, including but not limited to, an α-diazo ketone, α-halo ketone, pentafluorophenyl ester, or 2,4dinitrophenyl ester. In another group of embodiments, the anchoring moiety is a non-peptide affinity ligand for a target site.

BRIEF DESCRIPTION OF THE DRAWINGS

FIG. 1 illustrates the novel paradigm for drug design. This paradigm involves the creation of compounds comprising three discrete domains: an anchor, a linker and a drug (e.g., protein modifying motif). Henceforth, the compounds containing the three functional domains will be referred to as ALD "drugs". FIGS. 1A and 1B demonstrate the basic paradigm wherein an anchor binds to a protein in a specific manner and wherein specificity is given to the drug by the anchor moiety. The model is equally applicable for targeting drugs to any tissue containing a unique molecular protein or target.

FIG. 3 demonstrates the importance of the linking group on the function of the active agent

FIG. 7A shows the currents before $C_2$ application, following $C_2$ washout and subsequent to the application of 10 mM DTT. $C_2$ decreased whole-ell currents and this decrease was completely reversed by DTT. FIG. 7B shows the corresponding changes in Cd$^{2+}$ block before (squares) and after (circles) $C_2$ application and subsequent to DTT exposure (triangles). FIG. 7C illustrates that following DTT application to $C_2$ modified channels, the recovery from inactivation superimposes the recovery observed prior to $C_2$ anchoring.

FIG. 8A illustrates that Na$^+$ channel current inhibition by $C_5^O$, $C_{11}^O$ and $C_{14}^O$ shows significant use-dependence. Related to the use-dependence, FIG. 8B shows that the recovery from inactivation displayed two components for recovery from inactivation. The slow component observed in $C_5^O$, $C_{11}^O$ and $C_{14}^O$ modified channels is not observed in $C_2$ or benzocaine modified channels.

DETAILED DESCRIPTION OF THE INVENTION

I. General

Figure 1C:
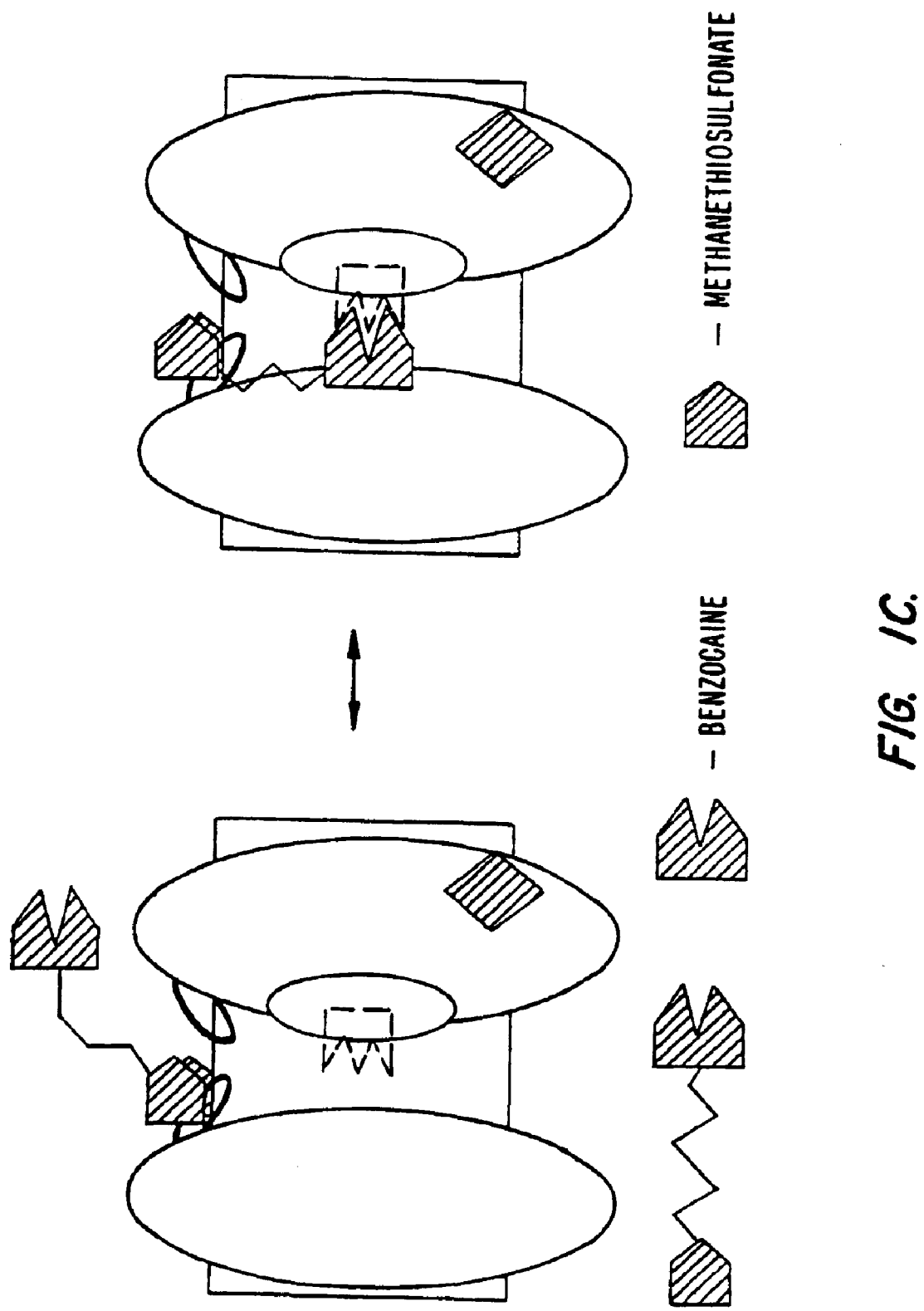
FIG. 1C illustrates that once localized by the anchor to the target protein, the drug will dynamically bind and unbind to its receptor.

Described herein are compounds and methods which are useful for specific delivery of drugs to a target selected from a group of functionally and structurally related homologous proteins.

A target-specific drug must discriminate between structural differences in related homologous proteins. Structurally, proteins consist of numerous functional domains attached and supported by "scaffolding" domains or regions. The scaffolding regions are responsible for ensuring that the functional domains (such as the active site) of the protein are maintained in the required spatial arrangement, thereby allowing them to function in the desired manner.

Generally, the scaffolding regions or domains of related proteins have the greatest degree of amino acid sequence diversification. There are at least two reasons for the differences seen in amino acid sequences within the scaffolding region between homologous proteins. First, these scaffolding regions do not commonly overlap structurally with the essential functional domains of the protein (i.e. the active site, phosphorylation domains, allosteric regulatory domains, substrate binding sites, etc.) and therefore changes in amino acid sequence do not affect the active site of the proteins. Second, since scaffolding regions are primarily required for structural support and are generally formed by α-helices and β-sheet structures, numerous amino acid substitutions are tolerated without major disruption of the overall scaffold structure and without untoward effects on the protein's function (Creighton, T. E., PROTEINS: STRUCTURE AND MOLECULAR PROPERTIES, W.H. Freeman and Co., New York, pp 201–269 (1993); and Branden, C. & Tooze, J., INTRODUCTION TO PROTEIN STRUCTURE, Garland Publishing Inc., New York, pp 11–77 (1991)). Therefore, the regions of homologous proteins which contain the majority of unique molecular structures are most often the scaffolding regions.

Nearly all drug design is based on modifying the functional properties of proteins. With related classes of proteins, this requires interaction of the drug with the highly conserved functional domains and the ability to develop tissue-specific agents is inherently lost. The present invention provides active agents which specifically target a single member of a homologous class of proteins expressed in a specific tissue (for example the $Na^+$ channel protein in heart). A generic description of the compounds is of three discrete domains: an anchor, a linker and a drug (e.g., protein modifying agent).

II. Definitions

The phrase "active agents" refers to the compounds of this invention. Active agents comprise an "anchor" or "anchoring group," a "linker" or "linking group," and a "drug."

The anchor, which recognizes a distinct molecular target in a protein found only in specific tissues, effectively delivers the active agent to the specific tissue/target. Once localized by the anchor to the target protein, the drug dynamically binds and unbinds to its binding site.

Active agents developed using this strategy can take advantage of both the anchor and the active portion of the drug in a synergistic relationship to enhance local concentration at the desired site. For example, some drugs have an inherent tendency to accumulate at a desired site and the use of a suitable anchor will further maintain the drug at the site and provide an apparent synergistic effect.

In another embodiment of the invention, a number of homologous proteins are expressed in different tissues of the body. Accordingly, anchors can be designed to bind to the homologous proteins by, for example, designing the anchor to bind to a conserved region of the protein, and target active agents to many tissues. Conserved regions or domains of proteins can be determined based on detailed molecular structural information derived from the published x-ray structures of the target proteins.

In yet another embodiment, the regions of the protein which interact with an anchor are not located immediately adjacent to the drug binding site of the protein. In one aspect of this embodiment, the anchor is located on one protein and the drug on another. In this instance, the linking group between the anchor and drug must be sufficiently long to allow both groups to interact with their target sites. For example, the functional domain of membrane proteins often interact and certain compounds of the present invention could have binding portions (anchoring groups and drugs) which bind to separate sites in the interacting proteins.

Still further, it is not necessary that the anchor be inert (as to pharmacological effects). For example, the anchor itself is a therapeutic agent which acts on one site, while the attached drug interacts at another site.

The term "administering" refers to exposing an animal, preferably a human to the compounds of this invention. The active agents of this invention may be administered systemically by injection, most preferably intravenously, but also intramuscularly, subcutaneously, intrathecally, intraperitoneally, into vascular spaces, or into joints, e.g., intraarticular injection. The dose will be dependent upon the properties of the active agent employed, e.g., its activity and biological half-life, the concentration of the active agent in the formulation, the site and rate of dosage, the clinical tolerance of the patient involved, the extent of disease afflicting the patient and the like, properties which are well within the skill of the physician to evaluate.

Administration can also be non-parenteral, e.g., inhalation, absorption or oral. As an inhalant, the active agent may be administered by aerosol to achieve localized delivery to the lungs. This is accomplished by preparing an aqueous aerosol, liposomal preparation or solid particles containing or derivatives thereof. A nonaqueous (e.g., fluorocarbon propellent) suspension could be used. Sonic nebulizers preferably are used in preparing aerosols. Sonic nebulizers minimize exposing the active agents to shear, which can result in degradation of the active agent.

Methods of rectal administration include, for example, suppositories and gelatin rectal capsules.

In a preferred embodiment, the method of administration is oral. The active agent can be delivered by the following methods: liquid solutions; capsules; sachets; or tablets; lozenge forms; as well as pastilles.

The phrase "covalent binding" refers to the sharing of electrons to fill a nucleus' electron octet. The result of a covalent bond is an increase in electron density between atomic nuclei.

The phrase "localization of drug" refers to the accumulation of a drug or an active agent of this invention in a specific tissue site.

The term "pharmaceutical composition" refers to formulations of various preparations. Parenteral formulations are known to those of skill in the art. Parenteral formulations containing therapeutically effective amounts of the active agents are either sterile liquid solutions, liquid suspensions or lyophilized versions, and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg or more.

Typically, the pharmaceutical compositions containing the active agents are administered in a therapeutically effective dose over either a single day or several days by daily intravenous infusion.

The pharmaceutical composition of the present invention may be administered in solution. The pH of the solution should be in the range of pH 5 to 9.5, preferably pH 6.5 to 7.5. The pharmaceutical composition optionally contains a suitable pharmaceutically acceptable buffer such as phosphate, tris (hydroxymethyl) aminomethane-HCl or citrate and the like. Buffer concentrations should be in the range of 1 to 100 mM. The pharmaceutical composition optionally contains a salt, such as sodium chloride or potassium chloride in a concentration of 50 to 150 mM. An effective amount of a stabilizing agent such as albumin, a globulin, a detergent, a gelatin, a protamine or a salt of protamine may also be included and may be added to a solution composition containing the active agent or to the composition from which the solution is prepared.

For pharmaceutical compositions suitable for inhalation, an aqueous aerosol is made by formulating an aqueous solution or suspension of the active agent together with conventional pharmaceutically acceptable carriers and stabilizers. The carriers and stabilizers will vary depending upon the requirements for the particular active agent, but typically include nonionic surfactants (TWEEN-20 OR -80®, PLURONIC-F128 OR -67®, or polyethylene glycol), innocuous proteins like serum albumin, or sorbitan esters, oleic acid, lecithin, amino acids such as glycine, buffers, salts, sugars or sugar alcohols. The formulations will be sterile. Aerosols generally will be prepared from isotonic solutions.

Pharmaceutical compostions suitable for oral use comprise: liquid solutions, such as an effective amount of the active agent suspended in diluents, such as water, saline or PEG 400; capsules, sachets or tablets, each containing a predetermined amount of the active agent, as liquids, solids, granules or gelatin; suspensions in an appropriate liquid; and suitable emulsions. Tablet forms include one or more of the following: lactose; sucrose; mannitol; sorbitol calcium phosphates; corn starch; potato starch; tragacanth; microcrystalline cellulose; acacia; gelatin; colloidal silicon dioxide; croscarmellose sodium; talc; magnesium stearate; stearic acid; and other excipients; colorants; fillers; binders; diluents; buffering agents; moistening agents; preservatives; flavoring agents; dyes; disintegrating agents; and pharmaceutically compatible carriers. Lozenge forms can comprise the active agent in a flavor, usually sucrose and acacia or tragacanth, as well as pastilles comprising the active agent in an inert base, such as gelatin and glycerin or sucrose and acacia emulsions, gels, and the like containing, in addition to the active agent, carriers known in the art.

Suitable pharmaceutical compositions for rectal administration include, for example, suppositories, which consist of the active agent with a suppository base. Suitable suppository bases include natural or synthetic triglycerides or paraffin hydrocarbons. In addition, it is also possible to use gelatin rectal capsules which consist of a combination of the active agent with a base, including, for example, liquid triglycerides, polyethylene glycols, and paraffin hydrocarbons.

III. Embodiments of the Invention

In one aspect, the present invention provides for a drug paradigm wherein active agents have an anchoring or targeting portion specific for a particular site or tissue. This paradigm is represented by the formula:

A-L-D in which A is an anchoring group, L is a linking group and D is a drug.

A. Anchoring groups

The drug paradigm of this invention requires tissue-specific anchors. Anchoring groups have the following properties: the anchor recognizes and binds to a structure that is unique to the target tissue. Consequently, the anchor will generally be designed to recognize and bind to regions of the target tissue which do not directly contribute to the formation of critical functional domains (e.g., part of the scaffolding region of proteins). As a result, anchoring group binding does not generally cause measurable alterations in target function. The precise region of the target to which the anchoring group binds should be a region of the target which is generally diverse and distinct between different members of functionally-related compounds.

Identification of potential anchoring group binding sites is accomplished in at least two ways. First, if the target is a protein, the sequences of homologous or closely related proteins are aligned to identify candidate amino acid sequences which are diverse and remote from the functional domains of the proteins. See, Creighton, T. E., PROTEINS: STRUCTURE AND MOLECULAR PROPERTIES, W.H. Freeman and Co., New York, pp 201–269 (1993); and Branden, C. & Tooze, J., INTRODUCTION TO PROTEIN STRUCTURE, Garland Publishing Inc., New York, pp 11–77 (1991)). This procedure is also used to assess the probable secondary structure of the candidate domains and their relative location (e.g., embedded in the protein's interior, on the protein's surface, in a hydrophobic region, or in a hydrophilic region). Second, protein crystal structures are used to identify the domains which are remote from the active site. Preferred sites are those sites located in the aqueous domains (hydrophilic regions) of the target protein.

Once the selected sequence, or site, has been identified, a compound which binds to the anchor group target protein with high affinity is created. One method of design involves the use of combinatorial chemistry to rapidly screen and identify compounds such as peptides, polysaccharides, oligonucleotides, etc. which preferentially bind to the targeted domain. Another method of design involves the use of computer modeling of protein structures.

Anchoring groups which are useful in the present invention are those groups which bind to a particular tissue or protein of interest in either a tight-binding non-covalent manner or in a covalent or irreversible manner. The anchoring groups are either targeting groups or simple functional groups which exert their "anchoring effect" once in position. In the case of targeted anchoring groups, the anchor is typically a group which acts as an affinity ligand for a specific tissue, protein or binding site. Affinity ligands are well known to those of skill in the art and include, but are not limited to, certain modified peptides or small modified proteins which have been altered to have reactive functional groups such as, for example, $\alpha$-halo ketones, $\alpha$-diazo ketones, or activated ester groups (e.g., 2,4-dinitrophenyl esters or pentafluorophenyl esters). When these peptides or other compounds bind to the target cell, the reactive groups form covalent bonds with the targeted binding site.

In the case of simple anchors which bind covalently to a site at or near a targeted cell, effective targeting will be accomplished via attachment of a drug which is known or predicted to localize or accumulate in the selected tissues. Examples of suitable covalent anchors include sulfhydryl-reactive groups (e.g., methanethiosulfonyl groups, dithiopyridyl groups, other reactive disulfides, and cystine), alkylating agents (e.g., $\alpha$-halo ketones, $\alpha$-diazo ketones), and acylating agents (e.g., activated esters such as 2,4-dinitrophenyl esters and pentafluorophenyl esters, and certain anhydrides). Other suitable anchoring groups are known to those of skill in the art.

Covalent attachment to a target site is not required for the compounds of the present invention. Non-covalent anchoring can take place via suitable electrostatic interactions with, for example, ammonium ion groups present in the target cell and carboxylic acid groups present in the anchoring group.

Another useful method of linking the active agents of this invention to proteins is through disulfide bonds (see, D. Willner, et al., *Bioconjugate Chem.* 4:521 (1993)). A number of reagents are available for chemical modification of cysteine sulfhydryl groups in proteins. One useful group is the thiosulfanates which react rapidly with thiols under physiological conditions (see T. W. Bruice and G. L. Kenyon, *J. Protein Chem,* 1:47 (1982)). Charged methanethiosulfonate reagents have also been used extensively to elucidate structural features of channel proteins and binding site topology (see, D. Fu, et al., *Biochemistry* 35:11278 (1996); M. H. Akabas, et al., *Neuropharmacology* 35:797 (1996); T. Kuner, et al., *Science* 258:307 (1992); D. A. Stauffer, and A. Karlin, *Biochemistry* 33:6840 (1994); M. Holmgren, et al., *Neuropharmacology* 35:797 (1996); and T. Kuner, et al., *Neuron* 17:343 (1996)).

Other embodiments of the present invention include the combination of sulfhydryl anchoring groups with dihydropyridine ion channel protein blockers. Experiments with cardiac myocytes demonstrate that sulfhydryl reactive agents bind to cardiac L-type sodium channel proteins. Therefore, with a linker of suitable length, the dihydropyridines are linked via sulfhydryl groups to the cardiac $Na^+$ channel proteins and specificially target and modify adjacent cardiac $Ca^{+2}$ channel proteins.

Still other embodiments of the present invention include the use of $\beta$-antogonists as anchoring groups linked to drug portions that modify $Na^+$, $Ca^{+2}$ or $K^+$ channel proteins. Currently available $\beta$-antagonists (or $\beta$-blockers) bind to the $\beta$-receptors with very high affinities and are extensively used in the treatment of acute and chronic heart failure. Attaching a channel protein modifying drug provides useful compounds for co-localizing the channel protein modifying drugs along with $\beta$-blocking compounds to the heart.

In another embodiment, FK-binding protein drugs are used as anchoring groups and linked to inhibitors of SR $Ca^{+2}$-release channel proteins for the treatment of malignant hyperthermia.

In yet another embodiment, carbohydrates are used as anchoring groups and linked to immunomodulatory drugs or to anti-viral drugs for the treatment of inflammation or viral diseases, such as HIV infection.

B. Linking groups

The linking groups used in the present invention are selected to impart a variety of properties to the targeted agent. In particular, the linking groups are selected to have a particular length which, due to entropic and enthalpic factors, governs the binding of the drug to its cellular target. The linking group is also selected to impart particular hydrophobic or hydrophilic properties to the active agent. For example, the linking group may be an alkylene chain (hydrophobic) or a polyethylene glycol chain (hydrophilic). In some embodiments, the linking group has a covalent or non-covalent connecting group to either the anchoring group or the drug portion (see FIG. 1A). Alternatively, the linking group consists of two portions which bind covalently or non-covalently to form one linker (see FIG. 1B).

The characteristics of the linking group often influence the properties of the targeting agent. If the linking group length is too short, anchoring does not allow the drug to bind to its receptor. In some embodiments, short linking group lengths allow interaction of the drug with its receptor, but only if the protein structure is strained by thermal motion (FIG. 1C). Accordingly, the potency of the drug, once anchored, may be lowered due to energetic destabilization of drug binding caused by mechanical strain. Alternatively, if the linker length is excessively long, drug binding rates are reduced due to the longer diffusion times necessary for the drug to encounter its receptor. Additionally, the relative polarity and degree of solvation of the linking group strongly influences the kinetics and energetics of drug binding subsequent to targeting agent anchoring.

In one embodiment, the linking groups are selected to connect the anchor and drug in a noncontinuous manner. For example, the linking group may be made of two parts connected via a pair of complimentary connectors as illustrated in FIG. 1B. In other words, the targeted agents can be comprised of two parts: a first part which is an anchor, linker and connector-1, and a second part which is a drug, linker and connector-2. Connector-1 and connector-2 are selected to be complimentary binding groups, for example, two complimentary oligonucleotides or an avidin-biotin pair. Other complementary binding groups are known to those of skill in the art.

In a preferred group of embodiments, the linking groups are those groups which are inert to proteolytic or other degredative processes in the body. Preferably, the linking groups are alkylene chains (more preferably having from about 2 to 30 methylene groups), aryl acetylenes, ethylene glycol oligomers containing 2–14 monomer units, diamines (e.g., 1,6-hexanediamine, 1,14-tetradecanediamine), diacids (e.g., succinic acid, glutaric acid and the like), or combinations thereof. In particularly preferred embodiments, the linking group is an alkylene chain of from two to 24 carbon atoms, more preferably from two to ten carbon atoms. The linking groups will typically have a functional group (i.e., hydroxyl, amino or carboxylic acid) at each terminus for the attachment of the anchoring or targeting moiety and for the attachment of the drug.

C. Drugs

The drugs used in the present invention can be any compounds which are appropriate medicaments for the particular disease to be treated. Often the drug is an antineoplastic agent, such as vincristine, doxorubicin, cisplatin, bleomycin, cyclophosphamide, methotrexate, streptozotocin, and the like. It is also be desirable to deliver anti-infective agents to cells in specific tissues by the present methods. The present invention is also useful for the selective delivery of other drugs including, but not limited, to local anesthetics, e.g., dibucaine and chlorpronazine; dihydropyridines ($Ca^{2+}$ channel blockers); β-adrenergic blockers, e.g., propranolol, timolol and labetolol; antihypertensive agents, e.g., clonidine and hydralazine; antidepressants, e.g., imipramine, amitriptyline and doxepim; anti-convulsants, e.g., phenytoin; antihistamines, e.g., diphenhydramine, chlorphenirimine and promethazine; antibacterial agents, e.g., gentamycin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

In another group of embodiments, the drugs are carbohydrates that bind to active sites in tissue or on bacteria or virus. These drugs may operate to prevent binding of host-related carbohydrates to tissues and stop the inflammation process or to prevent delivery of viral nucleic acids into the host cells through host cell receptors.

Other particular drugs which will be selectively administered by the method of the present invention are well known to those of skill in the art. In yet another embodiment, two or more therapeutic agents are administered simultaneously, where such agents produce complementary or synergistic effects.

Preparation of the above compounds is carried out by a variety of methods well known to one of skill in the art but preferably by standard synthetic methods (see, March, ADVANCED ORGANIC CHEMISTRY, 4TH ED., Wiley-Interscience, New York, 1992). For example, suitable linking groups with functionality (e.g., hydroxyl groups, thiols, carboxylic acid or amines) at each terminus are protected at one terminus to provide a single reactive terminus. Reaction of the single terminus with a suitable therapeutic agent provides a therapeutic agent with a covalently bound linking group (for example, via an ester, amide, disulfide, ether or other similar linkage). Subsequent deprotection at the distal end of the linking group and attachment of the anchoring group provides one of skill with the active agents of the present invention. In another embodiment, the method is reversed with the anchoring group added first and then the drug. Alternatively, the anchoring group and the drug are joined to a linker separately and the linkers joined to form the active agents of this invention.

D. Preferred Active Agents

In a particularly preferred embodiment, the targeting agents are compounds which bind to an ion channel protein, and have the formula:

A-L-D in which the A is an anchoring group selected from alkylthiosulfates in which the alkyl portion has from one to four carbon atoms; L is a linking group which is an alkylene group, optionally interrupted by one or more members selected from the group consisting of —O—, —S—, —NH—, or —NR—, wherein R is a lower alkyl group of from one to four carbon atoms; and D is a drug selected from the group of ion channel protein modifying agents.

Figure 2:
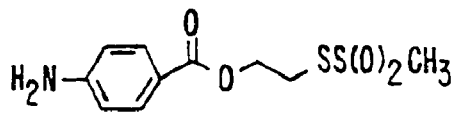
FIG. 2 illustrates prototype channel blockers of this invention. These agents contain an anchor which is comprised of a sulfhydryl reactive group linked through a hydrocarbon/ethylene glycol chain (i.e., ethylene group, $(CH_2)_2$ or ethylene glycol $CH_2$—CH—O) to a local anesthetic drug (i.e., benzocaine or lidocaine). Benzocaine is prototypic for class 1b agent with very rapid kinetics for binding and unbinding to $Na^+$ channels which is not tissue-specific; it binds equally to $Na^+$ channels throughout the body. The anchors take advantage of a unique cysteine which is present in the P-loop of cardiac $Na^+$ channels but not $Na^+$ channels in other tissues.
Figure 2:
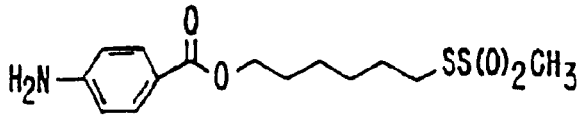
Figure 2:
Figure 2:
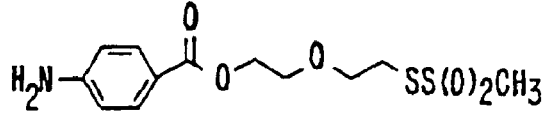
Figure 2:
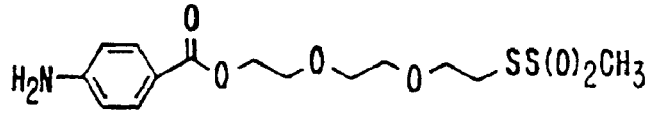
Figure 2:
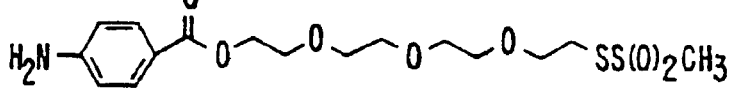
Figure 2:
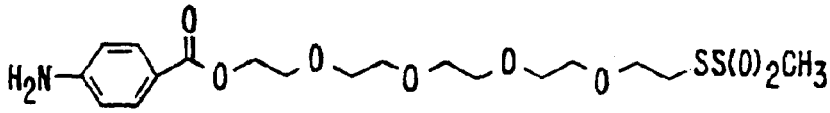
Figure 2:
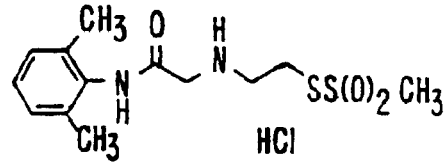
Figure 2:
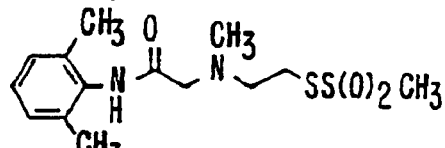
Figure 2:
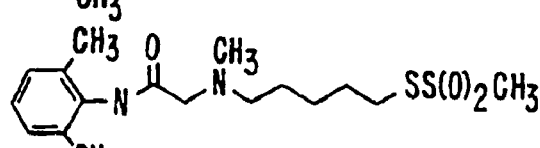
Figure 2:
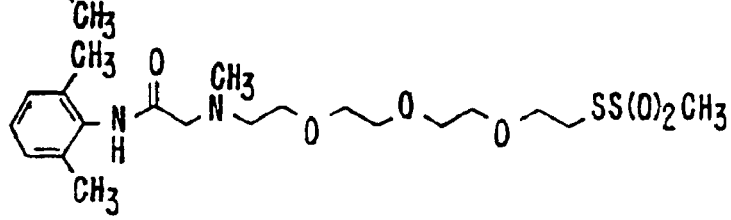

Specific embodiments within this group of targeted agents are provided in FIG. 2. These agents contain an anchor which is comprised of a sulfhydryl reactive group linked through a hydrocarbon/ethylene glycol chain (i.e. ethylene group, —(CH$_2$)$_2$— or ethylene glycol, —CH$_2$CH$_2$—O—) to local anesthetic agents (i.e. benzocaine or lidocaine derivatives). Benzocaine is a prototype for class 1b agents that have very rapid kinetics for binding and unbinding to Na$^+$ channel proteins and which is not tissue-specific, e.g., it binds equally to Na$^+$ channel proteins throughout the body. However, the anchors shown in FIG. 2 target benzocaine and other class 1b agents to cardiac muscle by taking advantage of a unique cysteine which is present in the P-loop of cardiac Na$^+$ channel proteins but not Na$^+$ channel proteins in other tissues. See, Backx, et al., *Science* 257:248–251 (1992). Also contemplated are analogs of the antiarrhythmic compound lidocaine and tocanide.

IV. Methods of Localizing Active Agents in Selected Tissues

In another aspect, the present invention provides methods of localizing an active agent in a selected tissue. According to these methods, the compounds provided above are administered to a suitable host. Preferred hosts include mammalian species, such as humans, non-human primates, dogs, cats, cattle, horses, sheep, and the like.

Many drugs that modify protein function bind with dissociation constants of about 100 nM to 10 µM. Optimally, the anchoring groups bind the chosen unique domains with about 100-fold higher affinity than the drugs bind to their targets. Therefore, the binding affinity of the anchoring groups will control localization or binding of the drug to the target protein and cell. Because the anchoring group has a much higher binding affinity for its target site, the drug portion will be tethered down and allowed to interact dynamically with its target site by repetitively binding and unbinding as illustrated in FIG. 1C.

Once anchored, the efficacy of drug action is dictated by the kinetics and the energetics of simultaneous interaction between both the anchoring group and the drug with their respective binding sites. As discussed above, the linker properties (e.g. length, bulkiness and polarity) are critical determinants of simultaneous interaction and therefore drug potency.

In still other embodiments, the binding site for the anchor and the active agent are located on different proteins. With a linking group of sufficient length, it is possible to anchor the drug onto a tissue-specific protein and deliver drugs which bind to or modify nearby proteins that are not themselves expressed in a tissue specific fashion. For example, β-adrenergic and α-adrenergic receptors (e.g., β1, β2, α1A etc.) are expressed in many tissues Accordingly, in one group of embodiments, active agents are provided in which suitable drugs are attached via linking groups to anchoring groups appropriate for the Na$^+$ channel protein which is linked to a β-blocker (or possibly an α-blocker). The modified β-blockers are useful in the treatment of heart disease and failure and would eliminate side effects associated with the non-specific binding of β-blockers to cells in other tissues.

Figure 3A:
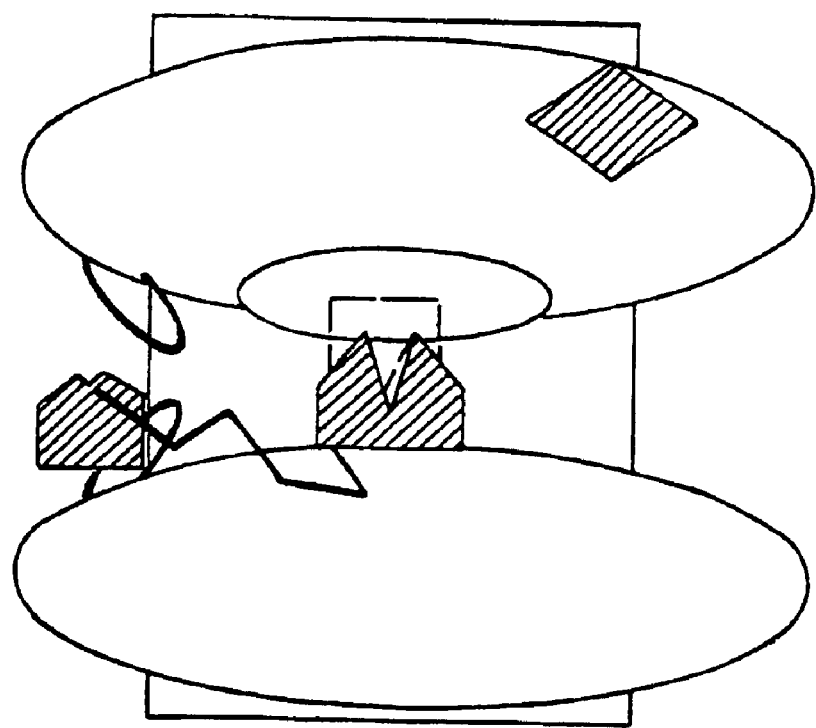
FIG. 3A illustrates linkers that are too short and too long.

In yet another embodiment, active agents are provided which bind to classes of ion channel proteins which are known to have a common ancestry. For example, voltage-gated ion channel proteins have common conserved structural motifs that have been replicated during evolution in K$^+$, Na$^+$ and Ca$^{2+}$ channel proteins. See FIGS. 3A and 3B. The lack of specificity of many drugs with respect to these different channel protein classes is due to the common motifs between different yet related channel protein types. For example, Ca$^{2+}$ channel protein blockers such as the dihydropryidines also modulate the activity of K$_{v1.3}$, other voltage-gated K$^+$ channel proteins, Na$^+$ channel proteins, etc. By linking drugs that lack specificity across the different classes of ion channel proteins with anchoring groups that are specific for cells with particular ion channel proteins, more selective active agents are created. In one embodiment, agents that are selective only for Na$^+$ channel proteins are created by linking a drug that alters the behavior of Na$^+$ and Ca$^{2+}$ channel proteins to an anchoring group that binds to or modifies Na$^+$ and K$^+$ channel proteins. The two active agents would, by virtue of their common binding to Na$^+$ channel proteins, localize the active agent to Na$^+$ channel proteins.

In yet another embodiment, the drug and the anchoring group both contain linker domains. These linker domains are then connected via a connecting group. In one particular embodiment, the connecting groups do not confer upon the linker domains a direct static physical connection between the anchoring group and the drug portion. Specifically, an active agent is created by a strong, direct and highly specific interaction within the linking group. For example, an active agent would comprise the anchoring group attached to another group labeled "A" while the drug portion is comprised of the drug linked to a group labeled "B". If "A" and "B" chemically interact, the anchoring group is linked to the drug and thereby delivers the drug to the specific target. A number of possible "A-B" pairs exist, for example short, digestion-resistant complimentary DNA sequences, lectins and lectin binding agents, and avidin and biotin agents.

The active agents described above are contacted with the target tissue by a variety of methods. Generally, the contact is made by direct application of the targeted drugs to the cells of the selected tissue. The application is made by topical, "open" or "closed" procedures. By "topical", it is meant the direct application of the targeted drugs to a tissue exposed to the environment, such as the skin, oropharynx, external auditory canal, and the like. "Open" procedures are those including incising the skin of a patient and directly visualizing the underlying tissue to which the targeted drugs are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. In one embodiment, the targeted drugs are administered to the peritoneum by needle lavage. In yet another embodiment, the targeted drugs are administered to the meninges or spinal cord by infusion during a lumbar puncture followed by appropriate positioning of the patient as commonly practiced for spinal anesthesia or metrazamide imaging of the spinal cord. Alternatively, the targeted drugs are administered through endoscopic devices.

In a preferred embodiment, the targeted drugs are administered orally or sublingually via either liquid solution, tablets, capsules, sachets or pastilles.

V. Ion Channel Protein Blockers

Without intending to bound by any particular theory or method of attachment, a detailed model is provided below for compositions which are useful in the treatment of ventricular and atrial arrhythmias.

Ventricular and atrial arrhythmias are routinely observed in diseased myocardium and are the leading cause of death (i.e., 50–80%) in patients with acute myocardial infarction, cardiomyopathic and cardiac hypertrophy. In acute myocardial infarctions (ie., heart attacks), the injury to the ischemic region of the heart commonly results in the development of arrhythmias which often result in death. Furthermore, unsustained ventricular tachycardia in patients with previous myocardial infarctions is closely associated with a mortality rate approaching 30% within two years. Clearly, therapies which specifically target cardiac tissue for patients at high risk of either acute cardiac ischemic events or subsequent infarction related arrhythmias would be of tremendous benefit for an enormous patient population (estimated to be between 2 and 3 million in the United States).

The present invention, therefore, provides methods to develop cardiac specific agents for the prophylactic treatment of patients at risk for myocardial ischemia and related arrhythmias.

The strategy used to treat cardiac arrhythmias involves the alteration of cardiac electrical activity through modulation of ion channel proteins. Channel proteins are enzyme proteins that catalyze the transfer of ions across the cell membrane. Ion channel proteins display two distinct functional properties: a pore (or hole within the protein) which allows the selective passage of one specific type of ion across the cell membrane (i.e., $K^+$ or $Na^+$ or $Ca^{2+}$ etc.); and gating of the openings of ion channel pores.

The gating in ion channel proteins is controlled by altering the availability of the pore to ions. This is effected by changes in voltage across the cell membrane. In other words, ion channel proteins undergo voltage-dependent changes in molecular structure which in turn tightly controls the availability of the pore or active site. The gating regions of channel proteins are distinct from the pore. A communication link is therefore present from the gating region which contains the voltage-sensors, to the channel pore which results in conformation changes in the structure of the protein.

The opening and closing of ion channel proteins is characterized by the probability of the channel being open ($P_O$). Gating is classically separated into "activation" and "inactivation" gating. As a result, $P_O$ can be written as:

$$P_O = P^a_O \times P^i_O$$

where $P^a_O$ and $P^i_O$ present the probabilities of the activation gate and the inactivation gate being open. These probabilities are voltage-dependent.

In response to changes in membrane voltage, channel proteins undergo time dependent changes in protein conformation (i.e., pore opening) that can be measured as time-dependent changes in current For example $Na^+$ channel proteins are closed at −80 mV, open following depolarization of the cell membrane (e.g., +20 mV) and subsequently close again.

Since channel proteins take on distinct molecular conformations with measurable functional properties, it is useful to classify the various conformations as distinct chemical entities. This procedure is routinely done in chemistry when determining reaction mechanisms. Specifically, if "A" reacts to form "B", it might form a number of distinct molecular intermediates in the process of going from A→B (e.g., A→C→D→B). In ion channel proteins, it is common to represent the various states of the channel protein with letter designations: "C"=closed deactivated, "O"=open, "I"= closed inactivated. To capture the essence of most voltage-gated channel proteins, it is assumed there is one closed, one open and one inactivated state. One scheme for gating is represented as:

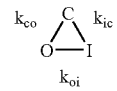

The rate constants for transition between the different states are voltage-dependent. As a result, at hyperpolarized potentials (e.g., −80 mV) the rate constants from "O" to "C" (i.e., $k_{oc}$) are very large while the rate constant for transition from "C" to "O" (i.e., $k_{co}$) are very small; as a result the channel proteins are closed (i.e., no current). Similarly $k_{ci}$ is very small while $k_{ic}$ is very large. Following depolarization, the $k_{co}$ becomes very large while $k_{oc}$ and $k_{ic}$ become very small; the channel proteins open and subsequently close. (i.e. channel proteins undergo conformational changes from "C" to "O" to "I"). Following repolarization (i.e., hyperpolarization of the cell) the channels return to "C" directly from "I", a process called recovery from inactivation. At any given voltage, the channel proteins will have a predetermined probability of being in the conducting state, "O," or the non-conducting states, "C" or "I". The probability of being in state "I" as a function of voltage is called the steady-state inactivation curve.

It is important to note that ion channel modifiers, such as local anesthetics, preferentially bind to the inactivated conformation of the channel protein. Since ion channel proteins are constantly changing their molecular structure in the process of gating, the modification of the channel by drugs like local anesthetics will depend of the activity of the channel. This is termed use-dependence. When local anesthetics bind to the inactivated state of the channel proteins, the channel proteins becomes trapped in the inactivated state. Therefore, membrane depolarization increases drug binding to the non-conducting inactivated state.

A. Cardiac-specific $Na^+$ and $K^+$ channel protein blockers

Many ion channel protein blockers have been tested in the treatment of ischemia related arrhythmias and death. Clinical trials with class 1c (e.g., combined $Na^+$ channel protein blockers/$K^+$ channel protein blockers) and class III (e.g., purely $K^+$ channel protein blockers) have proven to be disappointing. In a number of animal models of acute cardiac ischemia, the most effective agent against the development of ventricular tachycardia and fibrillation has been to be the type Ib class of drugs (e.g., $Na^+$ channel protein blockers). However, previous clinical trials with representative agents of this class of drugs (e.g., mexiletine) have demonstrated the drugs to not be viable therapeutic agents because of toxicity to tissues unrelated to the heart. Therefore, it would be highly desirable to develop class 1b agents that target specifically and exclusively cardiac $Na^+$ channel proteins. In view of the observation that the structure of cardiac $Na^+$ channel proteins are absolutely unique to the heart, the present invention provides class 1b antiarrhythmic drugs that are targeted to the heart through their cardiac-specific anchor groups.

A first prototype for these drugs is shown in FIG. 2. This agent contains an anchoring group comprised of a sulfhydryl reactive group linked through a hydrocarbon chain (i.e., ethylene group, $(CH_2)_2$) to a class 1b local anesthetic drug portion. Benzocaine is a prototypic class Ib agent with very rapid kinetics for binding to $Na^+$ channel proteins. The binding to $Na^+$ channel proteins is non-tissue specific. Heart channel proteins (in all species from which the amino acid sequence is available) have a free reduced sulfhydryl group in the channel pore (i.e., a cysteine residue in the pore) which is not present in other tissue-specific $Na^+$ channel proteins (Backx, et al., *Science* 257:248 (1992)). Another unique feature of the reactive sulfhydryl is that it is located on the extracellular face of the pore and is oxidized in the form of a disulfide linkage. The presence of this reactive sulfhydryl group, unique to heart Na$^+$ channel proteins provides a strong rationale for designing compounds with a sulfhydryl reactive anchor. As shown in FIG. 2, this invention provides for compounds which specifically bind to heart tissues and more specifically to heart Na$^+$ channel proteins.

In another embodiment, the anchoring group is targeted to the extracellular face of the pore in the N-terminal portion of the P-loop of domain I of the human cardiac Na$^+$ channel protein. This domain has a unique and distinct amino acid sequence from that of the nerve and skeletal muscle Na$^+$ channel proteins. Specifically, the target sequence is: GTNGSVEADGLVWESLDLYLSDPENYLLKNGTS (SEQ ID NO:1). To find anchoring groups, a polypeptide of SEQ ID NO:1 is made and used to screen for compounds binding to it. Combining the McClelland and Rumelhart methods (McClelland, J. L. & Rumelhart, D. E., EXPLORING IN PARALLEL DISTRIBUTED PROCESSING, Vol. 3, MIT Press, Cambridge, Mass., pp318–362 (1988) for secondary structure predictions with the Kneller, et al. method (Kneller, D. G., et al., *J. Mol Biol* 214:171 (1990)), a large portion of this sequence is predicted to form a helical structure which would be useful in predicting initial chemical structures to use in the screening assays. Compounds identified as high affinity binders are then tested in cultured cell lines (for example, human embryonic kidney cells (HEK cells)) which have been stably transfected with nucleic acid sequences which encode the human heart Na$^+$ channel protein and then tested in isolated human cardiac myocytes.

In another embodiment, the sequence: TIRGVDTVSRSSLEMSPLAPVNSHERRSKRRKRMSSGTEECGEDRLPKSDSEDGPRAMNHLSLTRGLSRTSMKPRSSRGSIFTFRRRDLGSEADFADDENSTARESESHHTSLLV PWPLRRTSAQGQPSPGTSAPGHALHGKKNSTVDCNGVVSLLGAGDPEATSPGSHLL RPVMLEHPPDTTTPSEEPGGPQMLTSQAPCVDGFEEPGAR (SEQ ID NO:2) is targeted for anchoring group binding. This peptide sequence is located in the I–II linker region on the intracellular face of the channel protein and has large sections which are predicted to form α-helical structures. Again, the secondary structure predictions are used to select classes of compounds which are likely to bind to the selected sequence. The screening procedure will involve the same steps as outlined above. In a particularly preferred embodiment, the screening is done in a high-throughput assay system.

The anchoring group is joined via a linker to a local anesthetic such as benzocaine or lidocaine. The linker length necessary for these compounds will be between 1–6 polethylene glycol units, more preferably between 1–4 polyethylene glycol units and most preferably between 1–3 polyethylene glycol units.

B. Cardiac- and smooth muscle-specific Ca$^{2+}$-channel protein blockers

Calcium channel blockers have been used as effective treatments for conditions such as hypertension and heart disease. Recently it has been shown that for some types of calcium channel protein blockers, there is little benefit of using these agents when longevity is the surrogate endpoint. This is due, in part, to activation of the sympathetic nervous system which is a side effect of the non-specific drugs.

For the treatment of hypertension it is desirable to block smooth muscle Ca$^{2+}$ channels and for the treatment of failing and diseased hearts it is desirable to block cardiac Ca$^{2+}$ channels. Because the smooth muscle L-type Ca$^{2+}$ channel is a distinct gene product from the cardiac channel proteins, active agents can be synthesized which specifically target smooth muscle Ca$^{2+}$ channel proteins.

In a preferred embodiment, cardiac-specific Ca$^{2+}$ channel protein blockers are designed so that the anchoring groups to bind to sequence MQDAMGYELPWVYFVSLVIF (SEQ ID NO:5) while for smooth muscle-specific blockers, the sequence VNDAVGRDWPWIYFVTLIII (SEQ ID NO:6) is targeted. These sequences are located in the P-loop of domain I. Another region in which these channel proteins differ is in the III–IV linker region. Therefore, in another embodiment, the sequence KHYFCDAWNTFDALIVVGSIVDIAITEVHP (SEQ ID NO:7) is targeted for the making of smooth muscle specific anchoring groups and the sequence KGYFSDPWNVFDFLIVIGSIIDVILSETNP (SEQ ID NO:8) for anchoring in the cardiac channel proteins. For smooth muscle specific agents, anchoring groups are targeted to the unique sequence RGTPAGLHAQKKGKFAWFSHSTETH (SEQ ID NO:9) which is located in the I–II linker. Once agents that bind to these sequences have been identified, they are linked to $Ca^+$ channel protein blockers, such as dihydropyridines (e.g., DHP) or verapamil via a polyethylene glycol linking group.

C. Skeletal muscle-specific local anesthetics

In another embodiment, the compounds of this invention are used in the treatment of myotonia muscle diseases such as paramyotonia congenita, hyperkalemic periodic paralysis and other disorders. These diseases result from lack of or mutations in the skeletal muscle $Na^+$ channel protein. Local anesthetics effectively correct the defective inactivation properties of these channels. Unfortunately, the use of these compounds is limited by their lack of specificity.

The anchoring groups of these agents target skeletal muscle-specific sequences, such as WYGNDTWYGNEMWYGNDSWYANDTWNSHASWATNDTFDW (SEQ ID NO:3). This sequence is absolutely unique to the skeletal muscle $Na^+$ channel proteins and is located on the extracellular face of the channel in the P-loop of domain I. Another sequence is EELEKAKAAQALEGGEADGDPAHGKDCNGSLDTSQGEKGAPRQSGSGDSGISDAM (SEQ ID NO:4) located in the I–II linker.

D. Nerve-Specific Local Anesthetics

Local anesthetics are also used for treating and preventing acute pain, particularly during surgical procedures including routine dental procedures. When applied locally to eliminate sensory inputs (and thereby pain), non-tissue-specific local anesthetics can enter the blood stream and produce detrimental generalized systemic effects on the heart and muscle. Risks associated with entry into the blood stream would be largely eliminated by using tissue-specific agents since much lower levels of the drug would be required. Tissue-specific local anesthetics would thereby have a much greater safety margin compared to agents that are currently used.

There are two unique sequences of human neuronal $Na^+$ channels that are targets as anchoring regions in these proteins. The sites are located at analogous positions to those described above for cardiac and skeletal muscle-specific agents. In the first, the residues in the first internal repeat domain are targeted. In the second, the residues in the I–II linker regions are targeted. Again, these sequences are unique to the human neuron $Na^+$ channels when compared to either the cardiac or skeletal muscle channels. As described above, these anchors are linked to local anesthetics like lidocaine and benzocaine.

V. Cardiac Specific β-Blockers

β-blockers, along with ACE inhibitors, are the only agents which have routinely been shown to reduce deaths in cardiac patients. However, patient compliance is a major problem since there are numerous undesirable side-effects resulting from actions of these agents on brain, nerve and other tissues. Cardiac-specific targeting eliminates these side-effects.

Since β-receptors are not uniquely expressed in heart tissue, cardiac specific β-blocker development requires anchoring to other nearby proteins. From $Na^+$ channel protein studies in human, guinea pig and rat myocytes, it is known that $Na^+$ channel proteins are expressed uniformly over the cell membrane. Therefore, in one embodiment, the anchoring group binding site is the $Na^+$ channel protein. The anchoring group is linked via a polyethylene glycol chain to any number of currently available β-blockers. The linker length required to allow interaction between the β-blocker attached on the $Na^+$ channel and the β-receptor is 40–50 Å in length or about 8–10 polyethylene glycol units.

In the preferred embodiment, the anchoring group is made using two separate strategies. First, the anchor is a sulfhydryl reactive group like methane-thiosulfonate (MTS) reactive groups or bromine linked to a polyethylene glycol chain. This anchoring group will react with the free cysteine which is found uniquely in the cardiac $Na^+$ channel. Second, the anchoring group will be a compound which is identified in combinatorial screening studies as binding to the extracellular face of the pore in the N-terminal portion of the P-loop of domain I of the human cardiac $Na^+$ channel protein. This domain has a unique and distinct ammo acid sequence from that of the nerve and skeletal muscle $Na^+$ channel proteins. Specifically, the target sequence will be: GTNGSVEADG-LVWESLDLYLSDPENYLLKNGTS (SEQ ID NO:1). To find anchoring groups, a polypeptide of SEQ ID NO:1 is made and used to screen for compounds binding to it. Combining the McClelland and Rumelhart methods (McClelland, J. L. & Rumelhart, D. E., EXPLORING IN PARALLEL DISTRIBUTED PROCESSING, Vol. 3, MIT Press, Cambridge, Mass., pp318–362 (1988) for secondary structure predictions with the Kneller, et al. method (Kneller, D. G., et al., *J. Mol Biol.* 214:171(1990)), a large portion of this sequence is predicted to form a helical structure which would be useful in predicting initial chemical structures to use in the screening assays. Compounds identified as high affinity binders are then tested in cultured cell lines (for example, human embryonic kidney cells (HEK cells)) which have been stably transfected with nucleic acid sequences which encode the human heart $Na^+$ channel protein, or in isolated human cardiac myocytes.

In another embodiment, the sequence: TIR-GVDTVSRSSLEMSPLAPVNSHERR-SKRRKRMSSGTEECGEDRLPKSDSEDGPRA MNHLSLTRGLSRTSMKPRSSRGSIFR-RRDLGSEADFADDENSTARESESHHTSLLV PWPLR-RTSAQGQPSPGTSAPGHALHGKKNSTVD-CNGVVSLLGAGDPEATSPGSHLL RPVMLEHPPDTTTPSEEPGGPQM-LTSQAPCVDGFEEPGAR (SEQ ID NO:2) is used to develop anchoring groups. This peptide sequence is located in the I–II linker region on the intracellular face of the channel protein and has large sections which are predicted to form α-helical structures. Again, the secondary structure predictions are used to select classes of compounds which are likely to bind to the selected sequence.

VI. Carbohydrates as Anchors for Drug Delivery

Carbohydrates play a critical role in many physiological and pathological functions. For example, carbohydrate binding has been shown to be involved in conditions including, but not limited to, diabetes, inflammation and other immunological processes, viral and bacterial diseases, and cancer metastases.

In inflammation and cancer metastases, the selectin family of adhesion molecules bind to specific carbohydrate ligands (Bevilacqua & Nelson, *J. Clin. Invest.* 91:379 (1993); Lasky, *Annu. Rev. Biochem* 64:113 (1995)).

Recent studies of the events involved in the inflammatory process have focused attention on the carbohydrate structures involved in the extravascular migration of neutrophils. This migration is a complex, multistage event, initiated by cell—cell recognition between carbohydrate cell-surface ligands (lectins) on the neutrophil and protein receptors such as P-selectin and E-selectin on the endothelial cell surface. This interaction leads to rolling of the neutrophil followed by adhesion and migration between the endothelial cells lining the blood vessel wall (Lasky, *Science* 258:964 (1992); Springer & Lasky, *Nature* 349:196 (1991); Springer, *Nature* 346:425 (1990); Butcher, *Cell* 67:1033 (1991); Hynes & Lander, *Cell* 68:303 (1992); and Stoolman, in CELL SURFACE CARBOHYDRATES AND CELL DEVELOPMENT, Fukuda (ed), CRC Press, Boca Raton, Fla., USA. 1992. p 71). Sialylated oligosaccharides such as sialyl $Le^x$ were fist identified as ligands for E- and P-selectin (Bevilacqua, et al., *Science* 243:1160 (1989); Lowe, et al., *Cell* 63:475 (1990); Phillips, et al., *Science* 250:1130 (1990); Walz, et al., *Science* 250:1132 (1990); Tiemeyer, et al., *Proc. Nat'l Acad. Sci. USA* 88:1138 (1991); and Springer & Lasky, *Nature* 349:196 (1991). Sulfated $Le^x$ and sulfated $Le^a$ were later isolated from an ovarian cystadenoma glycoprotein, and were found to exhibit comparable binding to E-selectin (Yuen, et al., *Biochemistry* 31:9126 (1992).

Carbohydrates are therefore useful to anchor anti-inflammatory drugs for site directed delivery. In one embodiment, Le- or Le-like oligosaccharides are used as the anchoring group. In one aspect of this embodiment, to prevent leukocyte binding, and thus migration through the vessel walls, the oligosaccharide anchor is joined via a linker group to a selectin antagonist. This active agent disrupts the cell—cell interaction between the neutrophils and the endothelial cells and prevents the rolling of the neutrophils along the vascular walls.

In other aspect of this invention, the anchoring group is a selectin mimetic or a compound that binds to the Le oligosaccharides on the surface of leukocytes. The linking group joins this anchor to an anti-inflammatory drug or toxin. These drugs and toxins include, but are not limited to, diflunisal, piroxicam, mefenamic acid, penicillamine, mesalamine, sulfasalazine, olsalazine, auranofin, gold sodium thiomalate, aurothioglucose, levamisole, azathioprine, cyclosporine, mycophenolate mofetil and tacrolimus. By specifically targeting the drugs to leukocytes, the effective amount of the drug or toxin will be lower and systemic side-effects will be less.

Carbohydrates can also be used as an anchor to deliver drugs specifically to pathogenic organisms such as bacteria and viruses. For example, many viruses use carbohydrates as binding sites that allow entry into a cell and subsequent infection. This is the case for influenza and HIV. To prevent infection, the carbohydrate anchors of this invention are linked to anti-viral or anti-bacterial drugs. In one aspect, well known antibiotics are the drugs targeted against bacteria. Against viruses, including HIV, the drugs include but are not limited to, clarithromycin, amandadine, rimantadine, ritonavir, indinavir, saquinavir mesylate, foscarnet sodium, nevirapine, stavudine, cidofovir, lamivudine, zidovudine, acyclovir, valacyclovir, gancyclovir, zaalcitabine and famcyclovir. The screening procedure will involve the same steps as outlined above. In a particularly preferred embodiment, the screening is done in a high-throughput assay system.

VII. High Throughput Screening

High throughput screening methods involve providing a library containing a large number of potential candidate compounds. Such "combinatorial chemical libraries" are then screened in one or more assays, as described above, to identify those library members (particular chemical species or subclasses) that display a desired binding activity. In the present invention, the identified compounds serve as conventional "lead compounds" or can themselves be used as potential or actual anchoring groups.

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks." For example, a linear combinatorial chemical library such as a polypeptide library is formed by combining amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487 (1991), Houghton et al., *Nature* 354:84 (1991)). Peptide synthesis is by no means the only approach envisioned and intended for use with the present invention. Other chemistries for generating chemical diversity libraries can also be used. Such chemistries include, but are not limited to: peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs, et al., *Proc. Nat. Acad. Sci. USA* 90:6909 (1993)), vinylogous polypeptides (Hagihara, et al., *J. Amer. Chem. Soc.* 114:6568 (1992)), nonpeptidal peptidomimetics with a β-D-glucose scaffolding (Hirschmann, et al., *J. Amer. Chem. Soc.* 114:9217 (1992)), analogous organic syntheses of small compound libraries (Chen, et al., *J. Amer. Chem. Soc.* 116:2661(1994)), oligocarbamates (Cho, et al., *Science* 261:1303 (1993)), and/or peptidyl phosphonates (Campbell, et al., *J. Org. Chem.* 59:658 (1994)). See, generally. Gordon, et al., *J. Med. Chem.* 37:1385 (1994), nucleic acid libraries, peptide nucleic acid libraries (see, e.g., U.S. Pat. No. 5,539,083) antibody libraries (see, e.g., Vaughn, et al., *Nature Biotech.* 14(3):309–314 (1996), and PCT/US96/10287), carbohydrate libraries (see, e.g., Liang, et al., *Science* 274:1520 (1996), and U.S. Pat. No. 5,593,853), and small organic molecule libraries (see, e.g., benzodiazepines, Baum, C&EN, Jan. 18, 1993 p. 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines 5,288,514, cyclopentane carboxylic acid (cispentacin) compounds (Jethwaney, D., et al., *Microbiology* 143:397 (1997) and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Any of the assays for anchoring groups described herein are amenable to high throughput screening. As described above, having identified the binding target sequence, the amino acid sequence is combined with the chemical library and binding partners are identified.

In one embodiment, the target sequence is bound to a microtiter plate or some other solid support. In the synthesis of the chemical library, the compounds of the library are labeled so that the compounds can be visualized. Such labels include but are not limited to: radionucliides, enzyme substrates, enzyme cofactors, biotin and other such appropriate labels known to those of skill in the art. The chemical library is then combined with the solid-phase amino acid sequence. After several washes, the compounds from the library that bound to the amino acid sequence are visualized through an appropriate method depending on the label utilized.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of a microplate in detector(s) appropriate for the assay. These configurable systems provide high throughput and rapid start up as well as a high degree of flexibility and customization. The manufacturers of such systems provide detailed protocols the various high throughput.

VIII. Pharmaceutical Compositions

The present invention also relates to a pharmaceutical composition comprising the active agents of the present invention in a pharmaceutically acceptable carrier. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend on the severity of the disease and the general state of the patient's health.

In one embodiment, the pharmaceutical composition is suitable for parenteral administration. Alternatively, the active agents of the present invention may be administered by various means appropriate for different purposes, for example, by direct application to tissues, either as a cream or emollient to externally availabe tissues or through lavage of internal organs, intravenously, intraperitoneally or intramuscularly, according to methods known in the art for other drugs. Preferably, the present invention relates to pharmaceutical compositions comprising an active agent of this invention and a pharmaceutically acceptable carrier, particularly such compositions which are suitable for oral administration.

Single or multiple administrations of the compositions may be administered depending on the dosage and frequency as required and tolerated by the patient. In any event, the composition should provide a sufficient quantity of the active agents of this invention to effectively treat the patient.

In one embodiment, the compositions for administration comprise a solution of the active agent, comprising the anchoring group linked to the drug, dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.01 to 100 mg per patient per day. Dosages from 0.1 up to about 1000 mg per patient per day may be used, particularly when the active agent is administered to a secluded site and not into the blood stream, such as into a selected tissue or organ. Actual methods for preparing parenterally administrable compositions will be known or apparent to those skilled in the art and are described in more detail in such publications as REMINGTON's PHARMACEUTICAL SCIENCE, 15TH ED., Mack Publishing Co., Easton, Pa., (1980).

In another embodiment, the active agent is encapsulated in liposomes, pharmaceutical delivery vehicles wherein the active agent is contained either dispersed or variously present in corpuscles consisting of aqueous concentric layers adherent to lipidic layers.

A variety of methods are available for preparing liposomes as described in, e.g., Szoka et al., *Ann. Rev. Biophys. Bioeng.* 9:467 (1980), U.S. Pat. Nos. 4,235,871, 4,501,728, 4,837,028, the text Liposomes, Marc J. Ostro, ed, Chapter 1, Marcel Dekker, Inc., New York (1983), and Hope, et al., *Chem. Phys. Lip.* 40:89 (1986), all of which are incorporated herein by reference.

Micelles containing active agents are prepared by methods which are well known to one of skill in the art For example, see U.S. Pat. No. 5,534,499 herein incorporated by reference.

In addition to liposomes and micelles, in another aspect of the invention, the active agents are administered as an emulsion or within a protein or other polymeric shell linked by disulfide bonds (U.S. Pat No. 5,560,933(herein incorporated by reference)). Both active agent-containing emulsions and polymeric shells are produced through sonication.

In topical preparations, the active agents are generally contained in urea-based emollients, petroleum-based ointments, and the like at concentrations of about 0.1 to 10,000 parts per million, preferably about 1 to 1000 parts per million, and most preferably about 10 to 100 parts per million.

Preferably, the active agent is formulated for oral use. If prepared in the form of a tablet, capsule or suppository, it is preferred that the active agent be present in an amount of about 0.1 mg per tablet, suppository or capsule. In such form, the capsule, suppository or tablet may also contain other conventional excipients and vehicles such as fillers, starch, glucose, etc. Actual methods for preparing parenterally, orally, and topically administrable compounds will be known or apparent to those skilled in the art and are described in detail in, for example, REMINGTON's PHARMACEUTICAL SCIENCE, 17th ed., Mack Publishing Company, Easton, Pa. (1985), which is incorporated herein by reference.

The following examples are offered solely for the purposes of illustration, and are intended neither to limit nor to define the invention.

IX EXAMPLES

Unless otherwise noted, all reagents are commercially available from such suppliers as Aldrich Chemical Co. (Milwaukee, Wis., USA). Abbreviations are used for common solvents and certain well-known reagents such as 4-dimethylaminopyridine (DMAP). Mass spectra were run on a VG Analytical ZAB-E double focusing mass spectrometer, with a source temperature of 200° C., source pressure of $4\times10^{-5}$ mbar, and a mass resolution of 1000.

Example 1

The Synthesis of 4-(4-aminophenyl)-4-oxo-3-oxabotyl methanethiosulfonate

See FIG. 2, Formula C2.

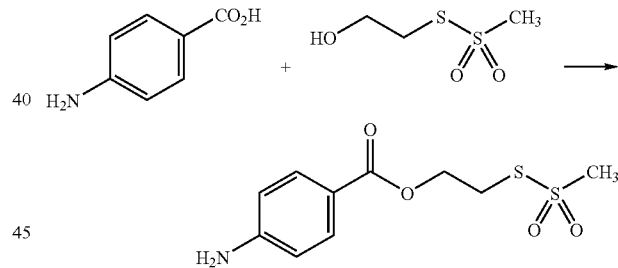

A solution of p-aminobenzoic acid (1.32 g; 9.6 mmol), 2-hydroxyethyl methanethiosulfonate (1 g; 6.4 mmol, prepared according to Boldyrev, et al., *Zh. Organic. Khim.* 3:37 (1967)), DCC (1.98 g; 9.6 mmol) and DMAP (61 mg; 0.5 mmol) in DMF (15 mL) was stirred at room temperature for 5 hours. It was then filtered, evaporated, and allowed to stand at room temperature for 2 days. Silica gel (8 g) was added and the mixture was evaporated to dryness. The residual powder was applied to a column of silica gel and then eluted with $CH_2Cl_2$/methanol (97:3). The factions containing 4-(4-aminophenyl)-4-oxo-3-oxabutyl methanethiosulfonate were combined, and evaporated to dryness. Crystallization from ethyl acetate afforded a white crystalline solid (670 mg; 2.44 mmol; 38% yield) with m.p. of 112–113° C. $^1$H NMR (500 MHz $(CD_3)_2SO$) δ7.63 (d, J=8.7 Hz, 2H), 6.56 (d, J=8.7 Hz, 2H), 6.00 (s, 2H), 4.44 (t, J=6.1 Hz, 2H); 3.56 (t, J=6.1 Hz, 2H), 3.56 (s, 3H). MS ($NH_3$ DCI): m/z 293 [$(M+NH_4)O^+$, 84%], 276 [$(M+H)^+$, 10%], 120 [100%].

Example 2

The Synthesis of 8-(4-aminophenyl)-8-oxo-7-oxaoctyl methanethiosulfonate

See FIG. 2, Formula C5.

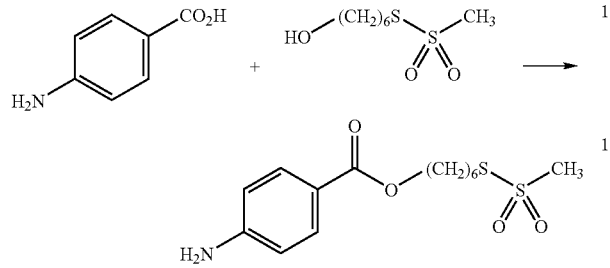

2.1 Preparation of 6-hydroxyhexyl methanethiosulfonate

A mixture of 6-bromo-1-hexanol (2.4 g; 0.013 mol) and sodium methane thiosulfonate (1.95 g; 0.0146 mol) in ethanol (30 mL) was heated at reflux for 20 hours. It was filtered, and 5 g silica gel was added to the filtrate, which was then evaporated to dryness. The residual powder was applied to a column of silica gel, which was eluted with ethyl acetate/hexane (7.5:2.5). The fractions containing 6-hydroxyhexyl methanethiosulfonate were combined and evaporated to dryness, to give a colorless oil (1.64 g; 8.0 mmol; 61% yield).

2.2 Preparation of Targeted Drug $C_6$

A mixture of p-aminobenzoic acid (1.11 g; 8.13 mmol), 6-hydroxyhexyl methanethiosulfonate (1.15 mg, 5.42 mmol), DCC (1.68 g; 8.13 mmol) and DMAP (66 mg; 0.50 mmol) in methylene chloride (50 mL) was stirred at room temperature overnight. The mixture was filtered and evaporated. The residue was allowed to sit at room temperature for 1 day, then dissolved in methanol. Eight grams of silica gel was added and the mixture was evaporated to dryness. The residual powder was applied to a column of silica gel (150 g) and eluted with $CH_2Cl_2$/methanol (9.75:0.25). The fractions containing product were combined, evaporated to dryness, and crystallized from ethyl acetate hexane to afford a white crystalline solid (280 mg; 0.845 mmol; 10% yield) with m.p. of 85–86° C. $^1$H NMR (500 MHz $(CD_3)_2SO$) $\delta$7.62 (d, J=8.7 Hz, 2H), 6.55 (d, J=8.7 Hz, 2H), 5.92 (s, 1H), 4.14 (t, J=6.5 Hz, 2H); 3.49 (s, 3 H), 3.19 (t, J=7.3 Hz, 2H), 1.72–1.64 (m, 4H), 1.41–1.39 (m, 2H). MS ($NH_3$ DCI): m/z 349 [$(M+NH_4)^+$, 32%], 332 [$(M\&H)^+$, 66%], 120 [100%].

Example 3

The Synthesis of 12-(4-aminophenyl)-12-oxo-11-oxadodecyl methanethiosulfonate See FIG. 2, Formula C10.

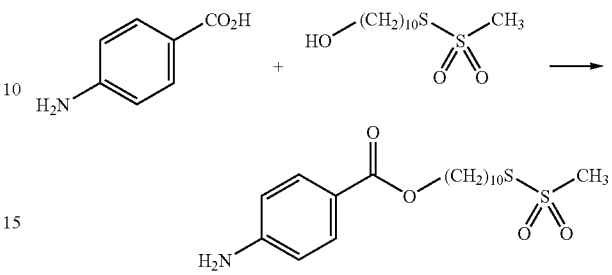

3.1 Preparation of 10-hydroxydecyl methanethiosulfonate

A mixture of 6-bromo-1-decanol (930 mg; 3.42 mmol) and sodium methane thiosulfonate (735 mg; 5.5 mol) in DMF (10 mL) was stirred at room temperature for 3.5 days. The solvent was evaporated, the residue dissolved in methanol, 3 g silica gel was added, and the mixture evaporated to dryness. The residual powder was applied to a column of silica gel and eluted with ethyl acetate/hexane (4:6). The fractions containing 10-hydroxydecyl methanethiosulfonate were combined, evaporated to dryness, to give a white solid (900 mg; 3.35 mmol; 85% yield).

3.2 Preparation of Targeted Drug $C_{10}$

A mixture of p-aminobenzoic acid (650 mg; 4.75 mmol), 10-hydroxydecyl methanethiosulfonate (850 mg; 3.17 mmol); DCC (980 mg; 4.75 mmol) and DMAP (31 mg, 0.25 mmol) in methylene chloride (40 mL) was stirred at room temperature overnight. The mixture was filtered and evaporated. Six grams of silica gel was added and the mixture was evaporated to dryness. The residual powder was applied to a column of silica gel (80 g) and eluted with $CH_2Cl_2$/methanol (9.75:0.25). The fractions containing product were combined, evaporated to dryness, and crystallized from ethyl acetate hexane to afford a white crystalline solid (530 mg; 1.37 mmol; 43% yield) with m.p. of 73–74° C. $^1$H NMR (500 MHz $(CD_3)_2SO$) $\delta$7.61 (d, J=8.7 Hz, 2H), 6.55 (d, J=8.7 Hz, 2H), 5.91 (s, 1H), 4.13 (t, J=6.6 Hz, 2H); 3.49 (s, 3 H), 3.17 (t, J=7.4 Hz, 2H), 1.68–1.62 (m, 4H), 1.35–1.26 (m, 12H). MS ($NH_3$ DCI): m/z 405 [$(M+NH_4)^+$, 7%], 388 [$(M\&H)^+$, 66%], 120 [100%].

Example 4

The Synthesis of 16-(4-aminophenyl)-16-oxo-3,6,9,12,15-pentaoxahexadecyl methanethiosulfonate See FIG. 2, Formula C14°.

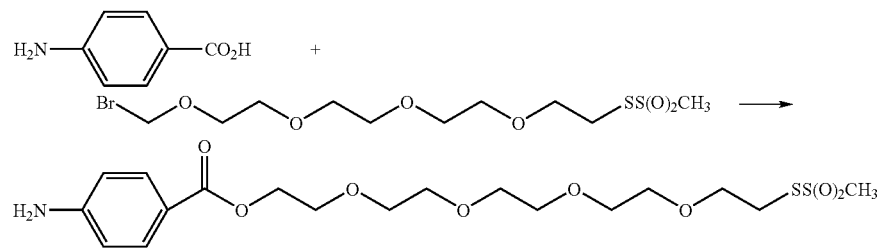

4.1 Synthesis of 1,14-dibromo-3,6,9,12-tetraoxatetradecane 1,14-dibromo-3,6,9,12-tetraoxatetradecane was made by the reaction of penta(ethylene glycol) with phosphorous tribromide (*J. Org. Chem*, 26:1991 (1961)).

4.2 Synthesis of 14-bromo-3,6,9,12-tetraoxatetradecyl methanethiosulfonate and 3,6,9,12-tetraoxatetradecane-1,14-diyl-bis-methanethiosulfonate 1,14-dibromo-3,6,9,12-tetraoxatetradecane (3.35 g, 9.2 mmol) and sodium methanethiosulfonate (2.48 g, 18.5 mmol) were dissolved in dry DMF (40 mL) and stirred at room temperature for 3 days. The solvent was evaporated. The residue was purified by column chromatography on $SiO_2$. Elution with ethyl acetate/hexane (9:1) afforded, after evaporation, 1-(14-bromo-3,6,9,12-tetraoxatetradecyl) methanethiosulfonate (0.85 g) as a pale yellow oil and tetraoxatetradecane-1,14-diyl-bis-methanethiosulfonate (useful as a cross linker) as a slightly yellow colored oil (1.64 g).

4.3 Synthesis of 16-(4-aminophenyl)-16-oxo-3,6,9,12,15-pentaoxahexadecyl methanethiosulfonate 4-aminobenzoic acid (0.145 g, 1.06 mmol) and 1-bromo-3,6,9,12-tetraoxatetradecyl methanethiosulfonate (0.42 g, 1.06 mmol) were dissolved in dry DMF (30 mL). Cesium carbonate (0.385 mg, 1.1 mmol) was added and the mixture was stirred at room temperature for 3 days. The solvent was evaporated. The residue was pied by column chromatography on $SiO_2$. Elution was with dichloromethane/methanol (100:3) and after evaporation, 16-(4-aminophenyl)-16-oxo-3,6,9,12,1 5-pentaoxahexadecyl methanethiosulfonate (0.120 g, 0.27 mmol; 25% yield) remained as a pale yellow oil. $^1H$ NMR (500 MHz, $(CD_3)_2SO$) δ 7.62 (d, J=8.7 Hz, 2H), 6.55 (d, J=8.7 Hz, 2H), 5.94 (s, br., 2H), 4.25 (t, J=4.8 Hz, 2H), 3.70–3.67 (m, 4H), 3.57–3.55 (m, 2H), 3.54–3.47 (m, 13H), 3.36 (t, J=5.9 Hz, 2H).

Example 5

The Synthesis of 13-(4-aminophenyl)-13-oxo-3,6,9,12-tetraoxatridecyl methanethiosulfonate See FIG. 2, Formula C11°.

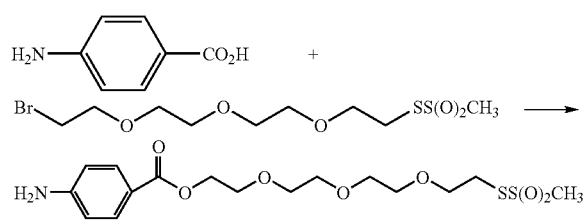

5.1 Synthesis of 1,11-dibromo-3,6,9-trioxaundecane, 11-bromo-3,6,9-trioxaundecyl methanethiosulfonate and 3,6,9-trioxaundecane-1,11-diyl-bis-methanethiosulfonate The compounds were prepared in a manner similar to that used for the preparation of the analogous compounds in Example 4.

5.2 Synthesis of 13-(4-aminophenyl)-13-oxo-3,6,9,12-tetraoxatidecyl methanethiosulfonate In a manner analogous to that above, the reaction of p-aminobenzoic acid (390 mg; 2.85 mmol), 1-(11-bromo-3,6,9-trioxundecyl) methanethiosulfonate (0.48 g, 2.79 mmol) and CsCl (946 mg, 2.96 mmol) yielded 13-(4-aminophenyl)-13-oxo-3,6,9,12-tetraoxatridecyl methanethiosulfonate (730 mg). $^1H$ NMR (500 MHz, $(CD_3)_2SO$) δ 7.62 (d, J=8.7 Hz, 2H), 6.55 (d, J=8.7 Hz, 2H), 5.94 (s, br. 2H), 4.25 (t, J=4.7 Hz, 2H), 3.70–3.67 (m, 4H), 3.57–3.55 (m, 2H), 3.54–3.51 (m, 9H), 3.36 (t,J =5.9 Hz, 2H).

Example 6

The Synthesis of 10-(4-aminophenyl)-10-ox-3,6,9-trixoxadecyl methanethiosulfonate See FIG. 2, Formula C8°.

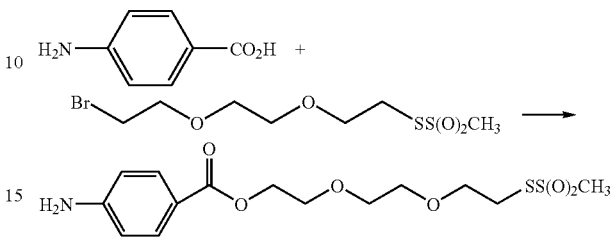

6.1 Synthesis of 1-(8-bromo-3,6-diaxoctyl) methanethiosulfonate and 1,8-3,6-dioxaoctyl-1,8-diyl-bis methanethiosulfonate These compounds were prepared in a manner analogous to that used for the preparation of 1-(14-bromo-3,6,9,12-tetraoxatetradecyl) methanethiosulfonate and 3,6,9,12-tetraoxatetradecane-1,1 4-diyl-bis methanethiosulfonate.

6.2 Synthesis of 10-(4-aminophenyl)-10-oxo-3,6,9-trixoxadecyl methanethiosulfonate In a manner analogous to that above, the reaction of p-aminobenzoic acid (473 mg; 4.90 mmol), 1-(8-bromo-3,6-dioxaoctyl) methanethiosulfonate (1.04 g, 3.39 mmol) and CsCl (1.17 g, 3.6 mmol) yielded 10-(4-aminophenyl)-10-oxo-3,6,9-trioxadecyl methanethiosulfonate (870 mg). $^1H$ NMR (500 MHz, $(CD_3)_2SO$) δ 7.62 (d J=8.6 Hz, 2H), 6,55 (d, J=8.6 Hz, 2H), 5.94 (s, 2H), 4.25 (t, J=4.8 Hz, 2H), 3.72–3.67 (m, 4H), 3.58 (s, br., 4H). 3.51 (s, 3H), 3.35 (t, J=5.9 Hz, 2H).

Example 7

The Synthesis of 7-(4-aminophenyl)-7-oxo-3,6,-dioxaheptyl methanethiosulfonate

See FIG. 2, Formula C5°.

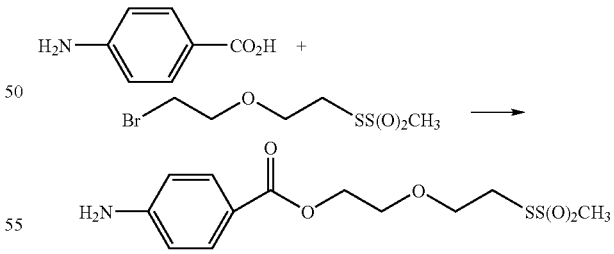

In a manner analogous to that above, the reaction of p-aminobenzoic acid (671 mg; 4.90 mmol), 1-(5-bromo-3-oxapentyl) methanethiosulfonate (1.29 g, 4.9 mmol) and CsCl (1.63 g, 5 mmol) yielded 7-(4-aminophenyl)-7-oxo-3,6-dioxaheptyl methanethiosulfonate (230 mg). $^1H$ NMR (500 MHz, $(CD_3)_2SO$) δ 7.62 (d, J=8.7 Hz, 2H), 6.55 (d, J=8.7 Hz, 2H), 5.95 (s, br., 2H), 4.27 (t, J=4.7 Hz, 2H), 3.77 (t, J=6.0 Hz, 2H), 3.73 (t, J=4.7 Hz, 2H), 3.50 (s, 3H), 3.39 (t, J=6.0 Hz, 2H).

Example 8

The Synthesis of 1-(2,6-dimethylphenyl)-2,8,8-trioxo-1,4-diaza-7,8-dithianonane See FIG. 2, Formula T$_2$.

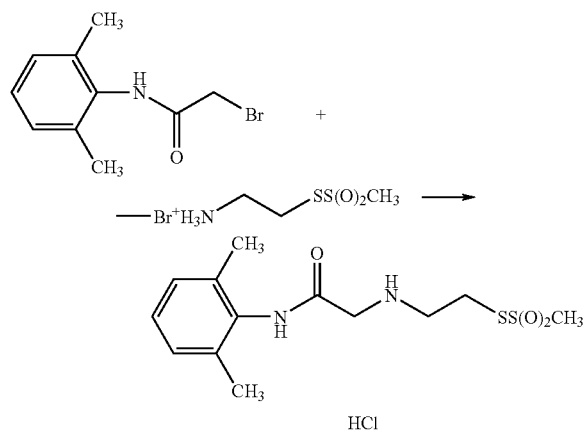

8.1 Preparation of 2-bromo-N-(2, 60-dimethylphenyl) acetamide

DCC (14.5 g; 70 mmol) was added to a cold solution of 2,6-dimethylaniline (8.5 g; 70 mmol) and bromoacetic acid (9.75 g; 70 mmol) in dry CH$_2$Cl$_2$ (400 mL) in portions over 30 min. The mixture was allowed to warm to room temperature overnight with stirring. It was then filtered, and the filtrate evaporated to dryness. The residual solid was dissolved in EtOAc (200 mL) and CH$_2$C$_2$ (200 mL). The mixture was filtered, and the filtrate evaporated to dryness to yield 2-bromo-N-(2,6-dimethylphenyl)acetamide (19 g).

8.2 Preparation of 1-(2,6-dimethylphenyl)-2,8,8-trioxo-1,4-diaza-7,8-dithianonane A solution of 2-bromo-N-(2,6-dimethylphenyl)acetamide (2 g; 8.26 mmol), aminoethyl methanethiosulfonate hydrobromide (2.8 g; 11.86 mmol), and diisopropylethylamine (4 mL; 23 mmol) in dry DMF (70 mL) was stirred at room temperature for 3.5 hours. The solution was evaporated and the residue purified by column chromatography on SiO$_2$. The column was eluted with CH$_2$Cl$_2$/MeOH/NH$_4$OH 95:5:0.2 and evaporation of the fractions containing the desired product afforded a pale yellow oil (1.66 g) which crystallized upon standing in the freezer. This was disolved in methanol/ether (1:1; 50 mL). A saturated solution of HCl in ether (4 mL) was added. The precipitated hydrochloride salt was filtered and dried to yield a light brown solid (1.15 g; 39% yield) with a melting point of 158–162° C. $^1$H NMR (500 MHz,(CD$_3$)$_2$SO) δ 9.93 (s, 1H), 9.32 (s, br, 2H), 7.10–7.07 (m, 3H); 4.08 (s, 2H), 3.61 (s, 3H), 3.54 (t, J=7.2 Hz, 2H), 3.40 (t, J7.2 Hz, 2H), 2.16 (s, 6H).

Example 9

The Preparation of 1-(2,6-dimethylphenyl)-4methyl-2,11,11-trioxa-1,4-diaza-10.11-dithiadodecane See FIG. 2, Formula L5

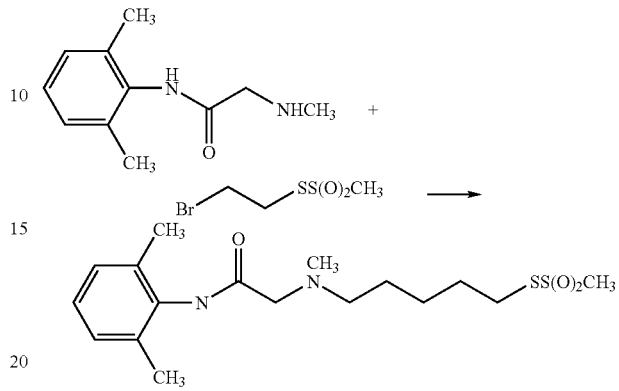

9.1 Preparation of N-(2,6-dimethylphenyl)-2-(methylamino) acetamide

N-methylglycine was converted to its N-Boc derivative using standard methodology (*J. Org. Chem.* 55:412 (1990)). N-Boc sarcosine (42 g, 0.22 mol) and 2,6-dimethylaniline (26.7 g, 0.22 mol) were dissolved in dichloromethane (1 L). The solution was cooled in an ice bath and dicyclohexylcarbodiimide (45.4 g, 0.22 mol) was added. The mixture was allowed to warm to room temperature and stirred overnight It was filtered, and the filtrate evaporated. The residue was purified by column chromatography on SiO$_2$. The column was eluted with ethyl acetate/hexane (3:7) and evaporation of the fractions containing the desired product afforded the amide as a light brown solid (48 g, 0.164 mol; 75% yield).

33% HBr in acetic acid (50 mid) was diluted by the addition of 200 mL acetic acid. This solution was added to a solution of the Boc protected amide (48 g, 0.164 mol) in acetic acid (150 mL). Water (500 mL) was added, followed by 33% HBr in acetic acid (50 mL). The solution was stirred overnight. The mixture was evaporated and water (300 mL) was added to the residual solid. The mixture was heated to 60° C. It was then cooled and filtered. The filtrate was evaporated and dissolved in water (500 mL) containing 65 g NaOH. The solution was then extracted with dichloromethane (3×400 mL). The combined organic extracts were washed with 150 mM NaCl (400 mL), dried over MgSO$_4$ and evaporated. The residue was solubilized in ether and washed with 10% NaOH (3×100 mL), then 150 mM NaCl (100 mL). The ether layer was dried over MgSO$_4$ and evaporated to yield N-(2,6-dimethylphenyl)-2-(methylamino)acetamide (25.9 g, 0.135 mol; 82% yield).

9.2 Preparation of 5-bromopentyl methanethiosulfonate and 1,5-pentanediyl-bis-methanethiosulfonate 1,5-dibromopentane (6.3 g, 27.4 mmol) and sodium methanethiosulfonate (5.87 g, 43.8 mmol) in dry DMF (100 mL) were stirred at room temperature overnight. The DMF was evaporated. The residue was purified by column chromatography on SiO$_2$. The column was eluted with ethyl acetate/hexane (1:1) and yielded, after evaporation 5-bromopentyl methanethiosulfonate (2.2 g) as a pale yellow oil, and 1,5-pentanediyl-bis-methanethiosulfonate (useful as a cross linker) as a white crystalline solid of melting point 71–72° C. (3.38 g).

9.3 Preparation of 1-(2,6-dimethylphenyl)-4-methyl-2,11,11-trioxo-1,4-diaza-10,11-dithiadodecane N-(2,6-dimethylphenyl)-2-methylaminoacetamide (1.55 g, 8.04 mmol), 5-bromopentyl methanethiosulfonate (2.1 g, 8.04 mmol) and diisopropylethylamine (2.8 mL, 16.08 mmol) in dry DMF (50 mL) were stirred at room temperature for 3 days. The reaction mixture was evaporated to dryness, and the resulting oil purified by column chromatography on $SiO_2$. The column was eluted with dichloromethane/methanol/ammonium hydroxide (98:2:0.1) and afforded, after evaporation, the methanethiosulfonate as an oil that crystallized upon standing. This was taken up in methanol/ether (1:3) and cooled. Addition of a solution of HCl in ether gave the hydrochloride salt as an off-white crystalline solid of melting point 183–186° C. (1.42 g, 3.46 mmol; 43% yield). $^1$H NMR (500 Mz, $(CD_3)_2SO$) δ 10.08 (s, br., 1H), 9.89 (s, br., 1H), 7.10 (s, 3H), 4.20 (s, br., 2H), 3.51 (s, 3H), 3.22 (t, J=7.3 Hz, 2H), 3.14 (s, br., 2H); 2.85 (s, 3H), 2.16 (s, 6H), 1.71–1.77 (m, 4H), 1.39–1.43 (m, 2H).

Example 10

The preparation of 1-(2,6-dimethylphenyl)-4methyl-2,17,17-triox-1,4-diaza-16,17-dithia-7,10,13-trioxaoctadecane See FIG. 2, Formula L11.

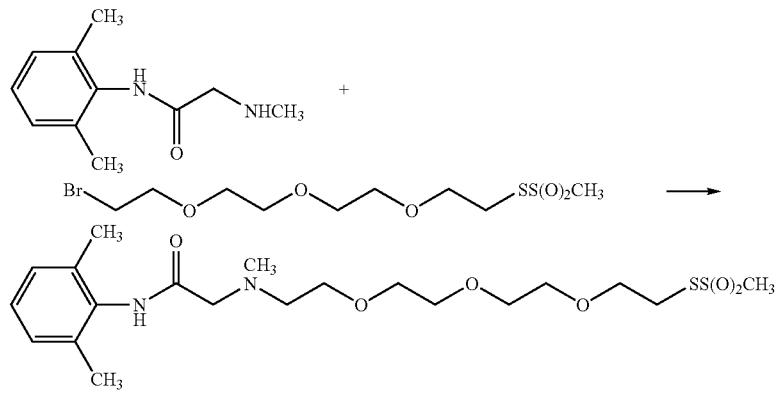

Using the same method as described in Example 9, N-(2,6-dimethylphenyl)-2-methylaminoacetamide (657 mg, 3.42 mmol), 1-(11-bromo-3,6,9-trioxundecyl) methanethiosulfonate (1.2 g, 3.42 mmol), and diisopropylethylamine (844 mg, 6.84 mmol) afforded 400 mg 1-(2,6-dimethylphenyl)-4-methyl-2,17,17-trioxo-1,4-diaza-16,17-dithia-7,10,13-trioxaoctadecane as a pale yellow oil. $^1$H NMR (500 MHz, (CD3)2SO) δ 9.11 (s, br., 1H), 7.05 (s, 3H), 3.66 (t, J=5.9 Hz, 2H), 3.57 (t, J=5.7 Hz, 2H), 3.52–3.50 (m, 5H), 3.46–3.44 (m, 4H), 3.42–3.41 (m, 2H), 3.35 (t, J=5.9 Hz, 2H), 3.19 (s, br., 2H), 2.69 (t, J=5.6 Hz, 2H), 2.39 (s, 3H), 2.13 (S, 6H).

Example 11

The preparation of 1-(2,6-dimethylphenyl)-4-methyl-2,7,7-trioxo-1.4-diaza-6.7-dithiaoctane See FIG. 2, Formula L2.

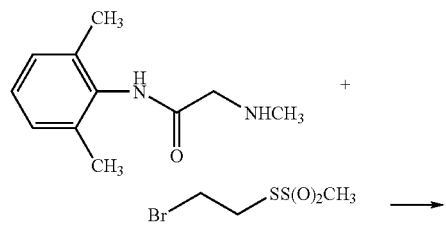

-continued

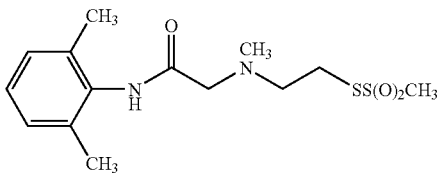

Using the same method as described previously, N-(2,6-dimethylphenyl)-2-methylaminoacetamide (1.6 g, 8.32 mmol), bromoethyl methanethiosulfonate (1.82 g, 8.32 mmol), and diisopropylethylamine (3.5 mL, 10 mmol) afforded 1-(2,6-dimethylphenyl)-4-methyl-2,7,7-trioxo-1,4-diaza-6,7-dithiaoctane. This was treated with HCl in ether to give the hydrochloride salt as a beige solid (580 mg). $^1$H NMR (500 MHz, (CD3)2SO) δ 10.26 (s, br., 1H), 10.05 (s, br., 1H), 7.13–7.08 (m, 3H), 4.23 (s, br., 2H), 3.62 (s, 3H), 3.62–3.53 (m, 4H), 2,89 (s, br., 3H), 2.16 (s, 6H).

Example 12

Evaluation of Site-Specific Therapeutic Agents

This example illustrates the evaluation of the site-specific therapeutic agents prepared in Examples 1–8.

12.1 Methods

Site-Directed Mutagenesis

Site-directed mutagenesis of the rat skeletal muscle sodium channel protein (μ1–2) was performed to create Y401C constructs. The mutations were introduced into a 2.5 kb SphI-KpnI cassette subcloned into pGEM7 (Promega, Madison, Wis.) using the oligonucleotide containing the appropriate base substitution.

Expression of Sodium Channel Proteins in Xenopus Oocytes

Oocytes were removed from adult female *Xenopus.laevis* frogs (NASCO, Fort Atkinson, Wis.; XENOPUS, Ann Arbor, Mich.) that had been anesthetized by immersion for 10–25 minutes in a 0.25% solution of tricaine (Sigma Chemical Co., St. Louis, Mo.) in tap water. A 5-fold excess of $Na^+$ channel protein β subunits compared to α subunits minimized the altered gating properties of $Na^+$ channel proteins in oocytes. Injected oocytes were incubated at 22° C. for 24–48 hr prior to recording.

Electrophysiological Recording

For oocyte recordings, whole-cell currents were recorded at room temperature (approximately 23° C.) using a two-electrode voltage-clamp with 3 M KCl in the pipette and a bath solution containing: 96 mM NaCl, 4 mM KCl, 1 mM MgCl$_2$, 1 mM CaCl$_2$ and 10 mM HEPES (pH=7.6). Electrode pipettes were fabricated from 1.2 mm outer diameter thin-walled borosilicate glass (TW120F-6, World Precision Instruments Inc., Sarasota, Fla.) pulled on a Sutter puller (model P-87). Pipette tips were broken to a diameter of approximately 0.1 mm and plugged with agar made with 3 M KCl for a final resistance of 1–4 MΩ. The circuitry of the amplifier compensated for electrode series resistance (Oocyte Clamp OC-725A, Warner Instruments Inc., Hampden, Conn., USA). Leak subtraction was accomplished using a P/8 protocol from a holding potential of −120 mV. Current was filtered at 2 kHz and digitized at 10 kHz using an IBM-compatible computer, a Warner analog-digital interface (model PP-50 Lab 1), and custom acquisition software. In order to minimize difficulties associated with voltage-clamping oocytes expressing large numbers of channel proteins, whole-cell recordings were limited to oocytes expressing less than 5 μAmps of peak current.

Similar recording methods were used with isolated rat ventricular myocytes using the patch-clamp recording technique.

The desired concentrations of local channel protein anesthetic drugs in ND96 were introduced to the bath by perfusion with at least 30 mL (bath volume=0.6 mL). Total bath exchange took less than 3 minutes and the drugs were allowed to equilibrate with the oocytes for a minimum of 6 minutes prior to recording.

Voltage Protocols

Current-voltage relationships were produced by stepping the membrane potential from −60 to +50 mV by increments of 5 mV from a holding potential of −80 mV. A repetition frequency of 0.2 Hz was used for such voltage families. Steady-state activation curves of whole-cell currents were calculated from the current-voltage relationships by scaling the peak currents by the net driving force (i.e., V−$E_{rev}$) using the equation g=I/(V−$E_{rev}$) where $E_{rev}$=+45 to +60 mV. Steady-state fast-inactivation curves were constructed by normalizing the current recorded in test pulses to −10 mV following 50 msec prepulses to voltages ranging from −100 to −10 mV. A repetition frequency of 0.2 Hz was used for the steady-state inactivation protocol. Recovery from inactivation was assessed using a two-pulse protocol, in which identical depolarizing voltage pulses to −20 mV for 50 msec were applied to oocytes before (conditioning) and after (test) a variable duration repolarization to −80 mV (recovery potential). The peak current evoked by the second (test) depolarization was normalized to the amplitude of the first (conditioning) depolarization and represents the fraction of channel proteins that had recovered from inactivation during the interpulse recovery period.

12.2 Evaluation of Site-Specific Agents

Figure 3A:
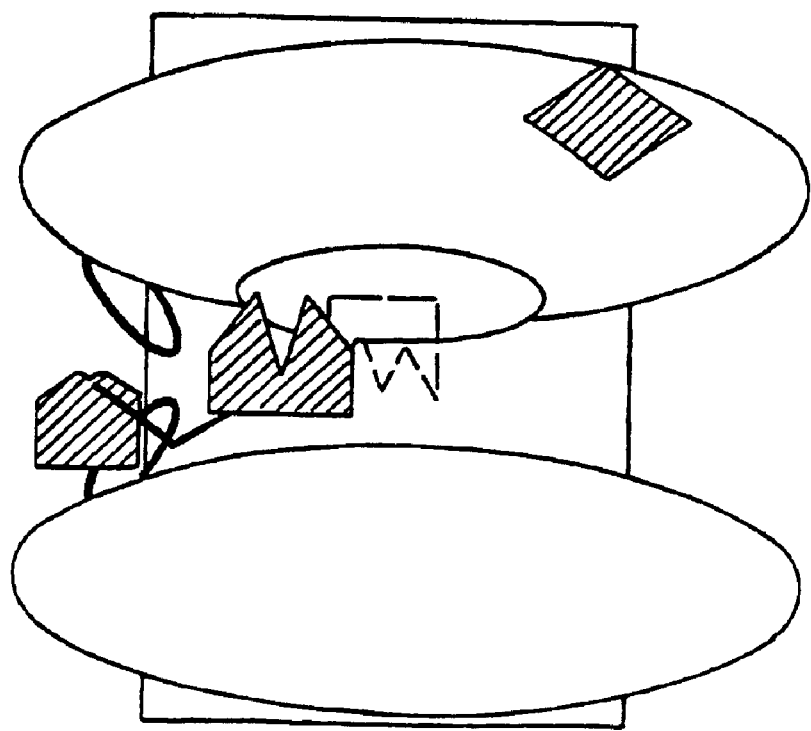
Figure 3B:
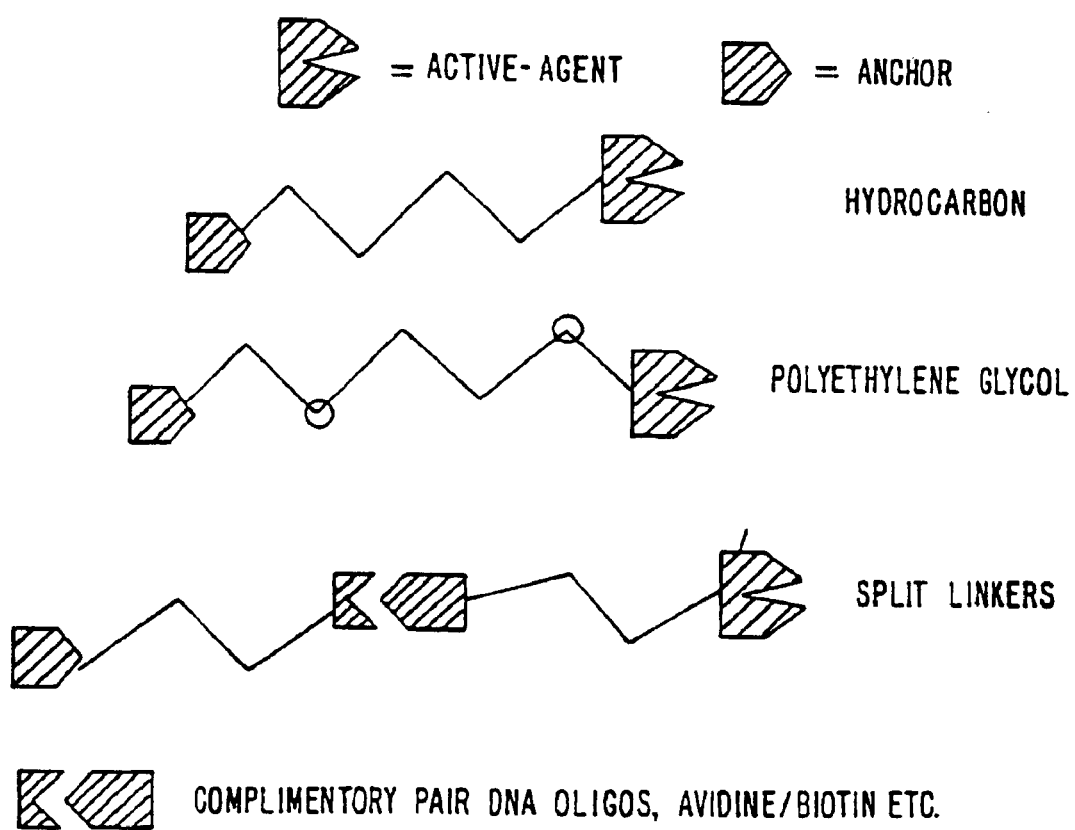
FIG. 3B illustrates the types of linkers encompassed by this invention: straight chain hydrocarbons; polyethylene glycols; and bifunctional linkers, i.e., linkers that are connected by complementary binding pairs.
Figure 4:
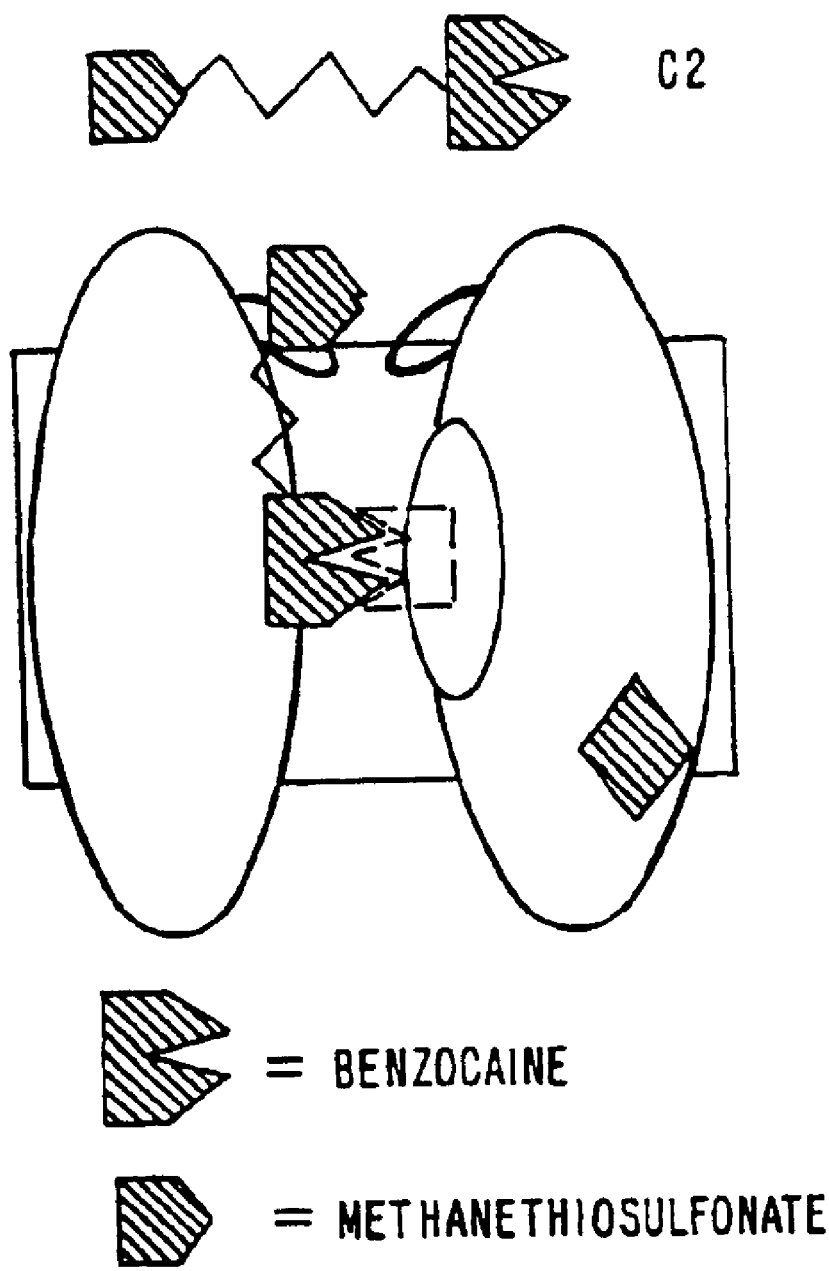
FIG. 4 illustrates the principle that anchoring the drug to a channel protein increases the effective concentration of the drug in the vicinity of the channel protein.
Figure 5A:
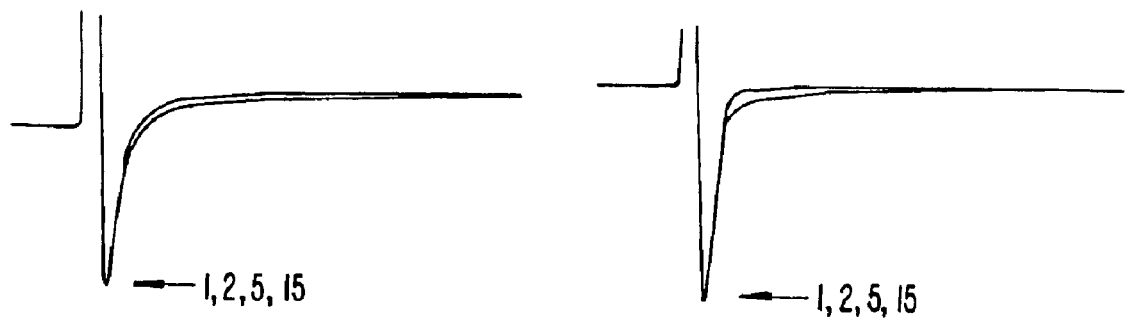
FIG. 5 shows the effect of benzocaine and lidocaine on Y401C Na$^+$ channels. The left panel in FIG. 5A shows the changes in whole-cell current following depolarization to –20 mV from a holding potential of –80 mV after the application of 500 µM benzocaine recorded in oocytes expressing Y401 C (left) and HH1 (right) channels. The currents recorded during the 1st, 2nd, 5th and 15th depolarization are numbered in FIG. 5. The recovery from inactivation curves are illustrated in FIG. 5B before (squares), during (circles) and after (open triangles) the application of 500 µM benzocaine for Y401C (left) and HH1 (right) channels. In contrast.
FIG. 5C shows typical whole-cell currents recorded sequentially (numbered) following repetitive membrane depolarization to –10 mV at a rate of 10 Hz following 30 µM lidocaine application for Y401C (left) and HH1 (right). As expected from the slower kinetics of drug binding, lidocaine shows use-dependent block in both channel types.
FIG. 5D shows the recovery inactivation before (squares), during (circles) and after (triangles) the application of lidocaine. The recovery after application of lidocaine has two kinetic components: The first rapid phase of the recovery is identical to recovery in the absence of lidocaine ($t_{fast}$=5.0 msec and 2.9 msec in Y401C channels while being 16.11 msec and 18.3 msec in HH1 channels with and without lidocaine). The second slow component ($t_{slow}$= 365 msec in Y401C and 763 msec in HH1) is not seen in the absence of drug and reflects the slow kinetics of lidocaine unbinding from the channel.
Figure 5B:
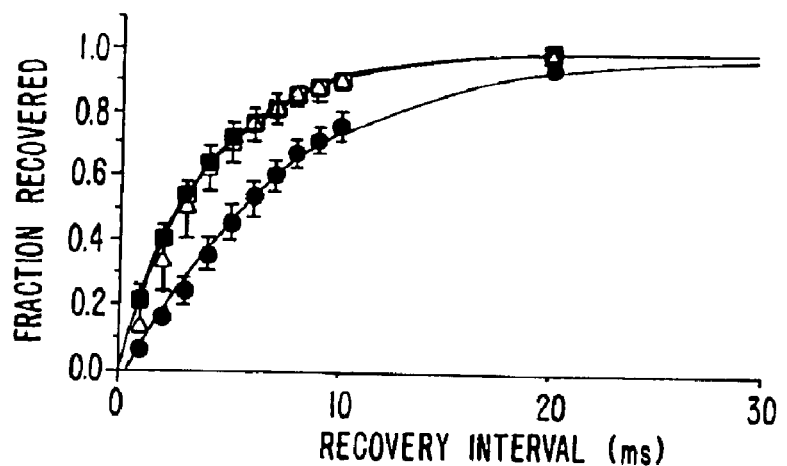
Figure 5B:
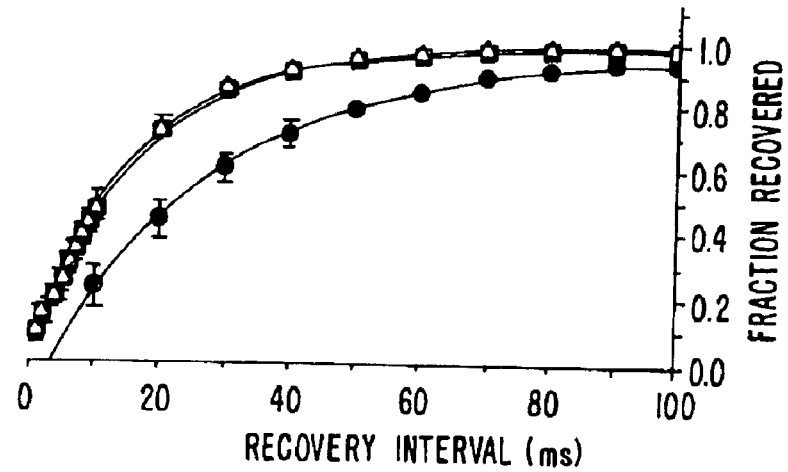
Figure 5C:
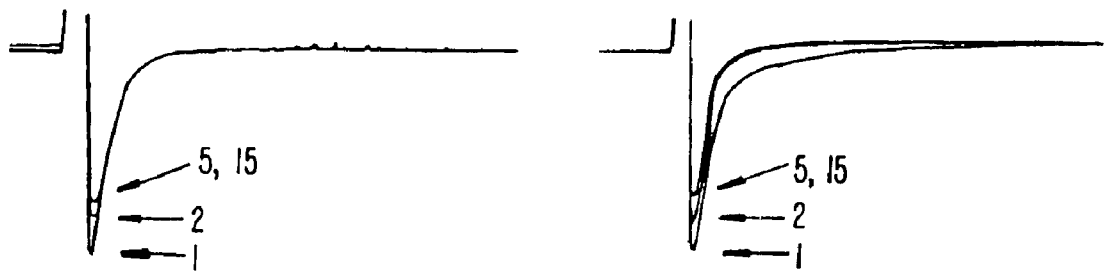
Figure 5D:
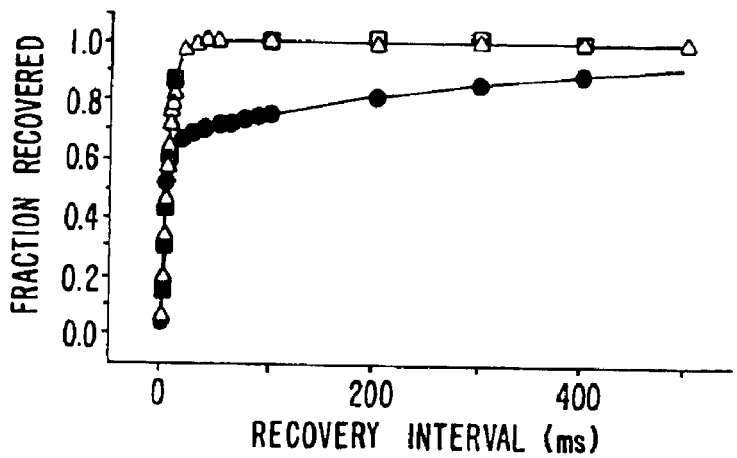
Figure 5D:
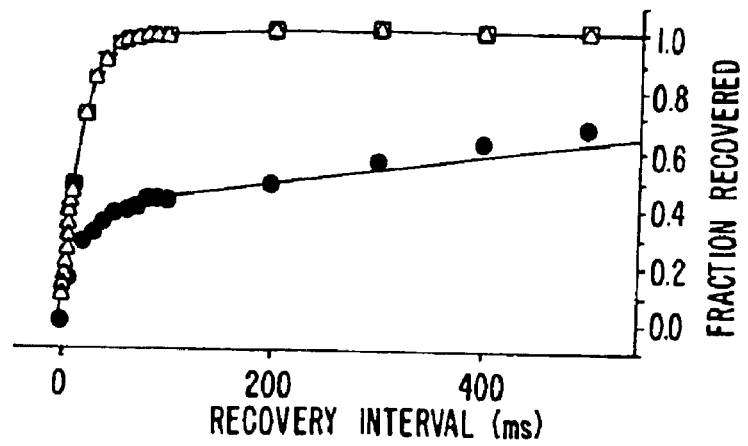
Figure 5E:
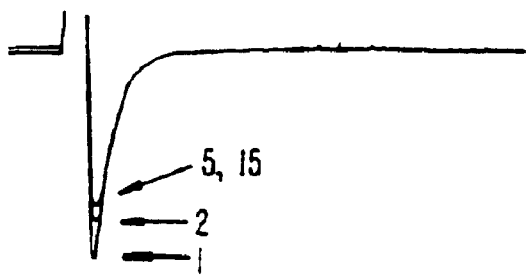
Figure 5F:
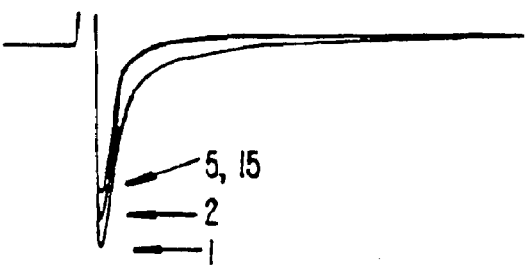
Figure 5G:
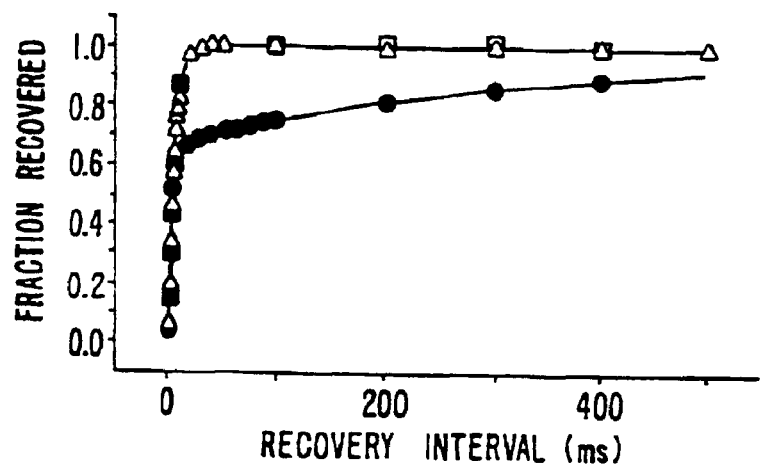
Figure 5H:
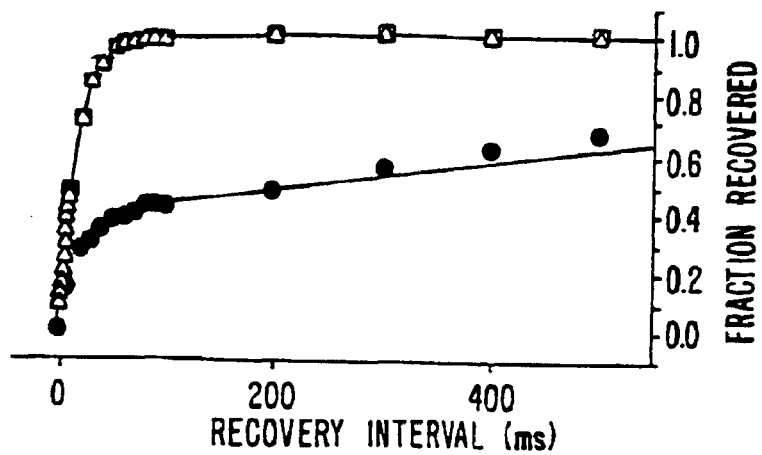
Figure 6:
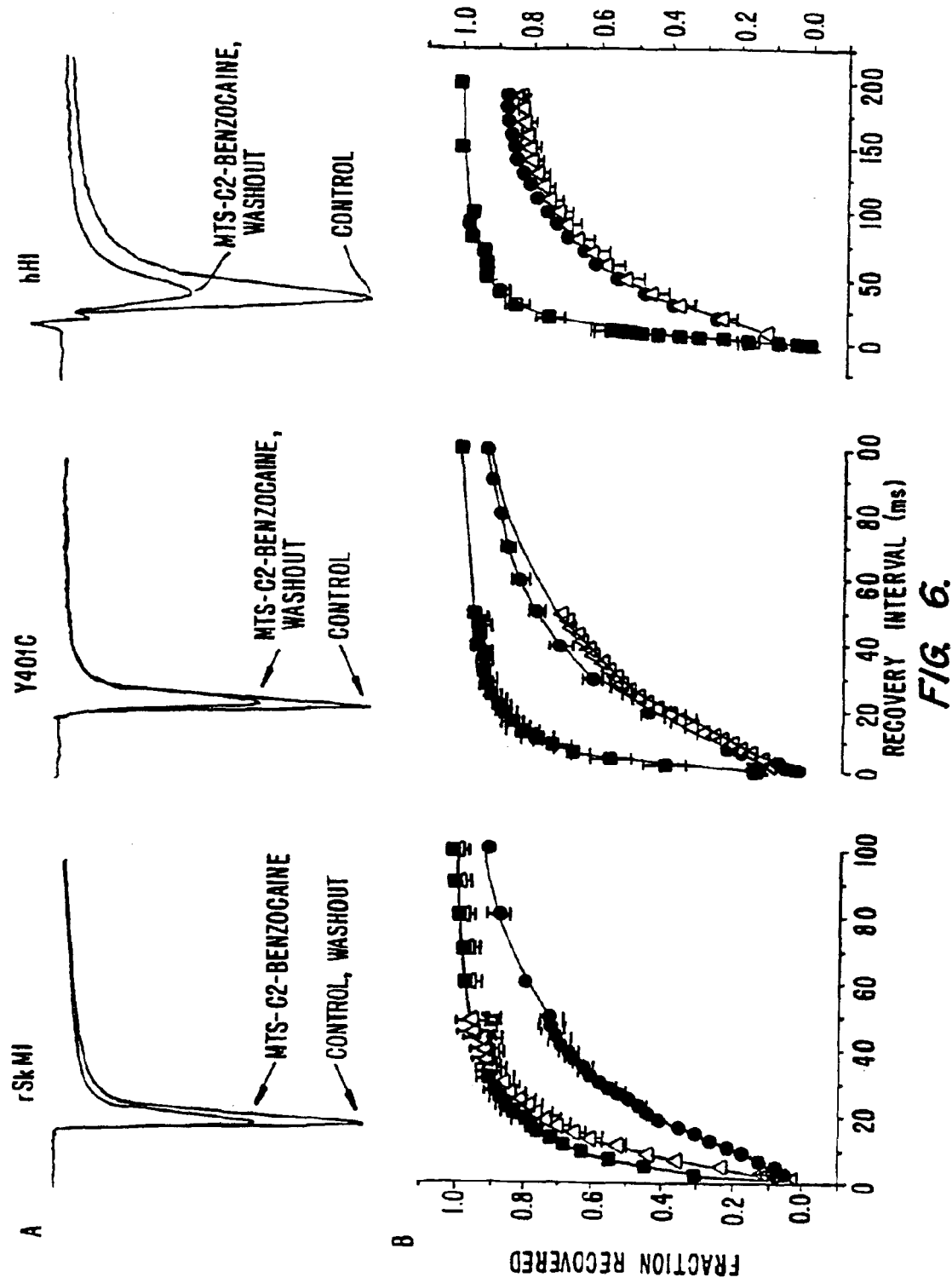
FIG. 6 depicts results of $C_2$ application. $C_2$ is an agent which contains an anchor comprised of a sulfhydryl reactive group linked through a two carbon chain (i.e., ethylene group, $(CH_2)_2$) to a benzocaine-like drug. The currents are measured in skeletal muscle (rSkM1), Y401C and HH1 Na$^+$ channels recorded in oocytes following depolarization to –10 mV from a holding potential of –80 mV. The results are shown before the application of $C_2$ (squares), during the application of 500 µM $C_2$ (circles) and after the washout of $C_2$ (triangles). In rSkM1 channels, the time constant for recovery from inactivation was 6.5 msec before $C_2$, 56.7 msec in the presence of $C_2$ and 13.7 msec after $C_2$ washout. On the other hand, the time constants for Y401C channels were: 4.97 msec before, 39.0 msec during and 40.4 msec after $C_2$ application. For HH1 channels the time constants were: 13.1 msec before, 45 msec during and 66 msec after the application of $C_2$.
Figure 7:
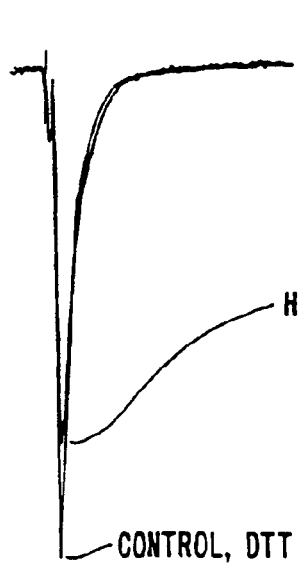
FIG. 7 illustrates that the methanethiosulfonate of $C_2$ is anchored via the unique cysteine in the pore of cardiac Na$^+$ channels.
Figure 7:
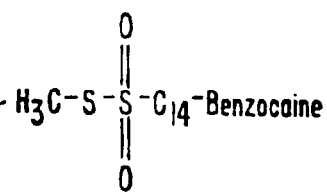
Figure 7:
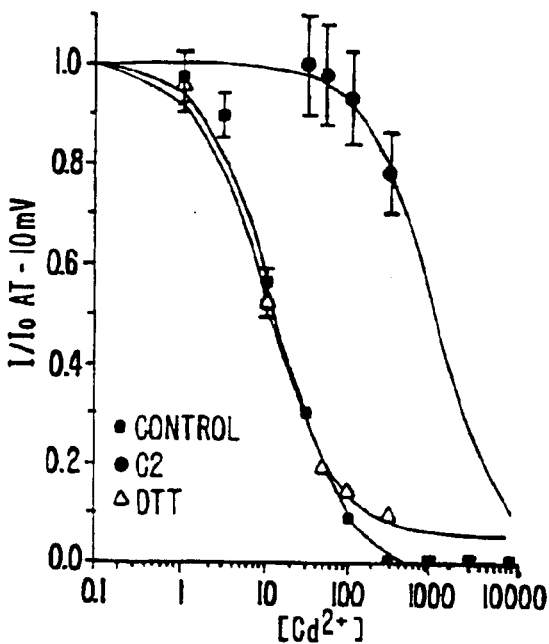
Figure 7:
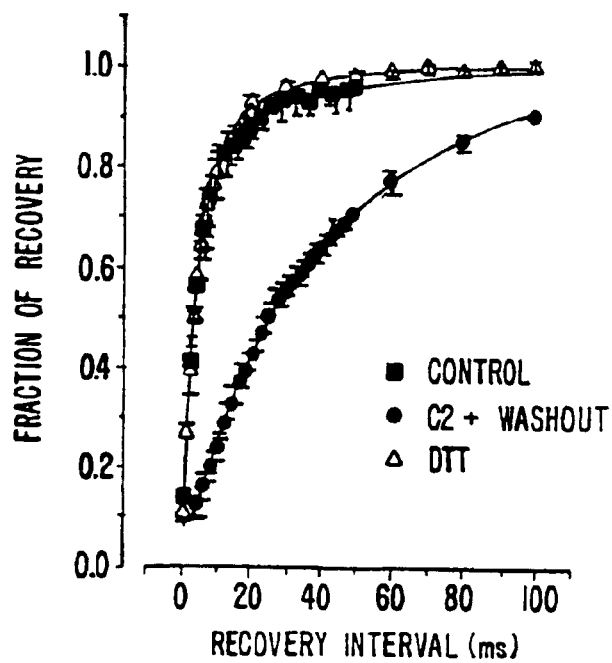
Figure 8:
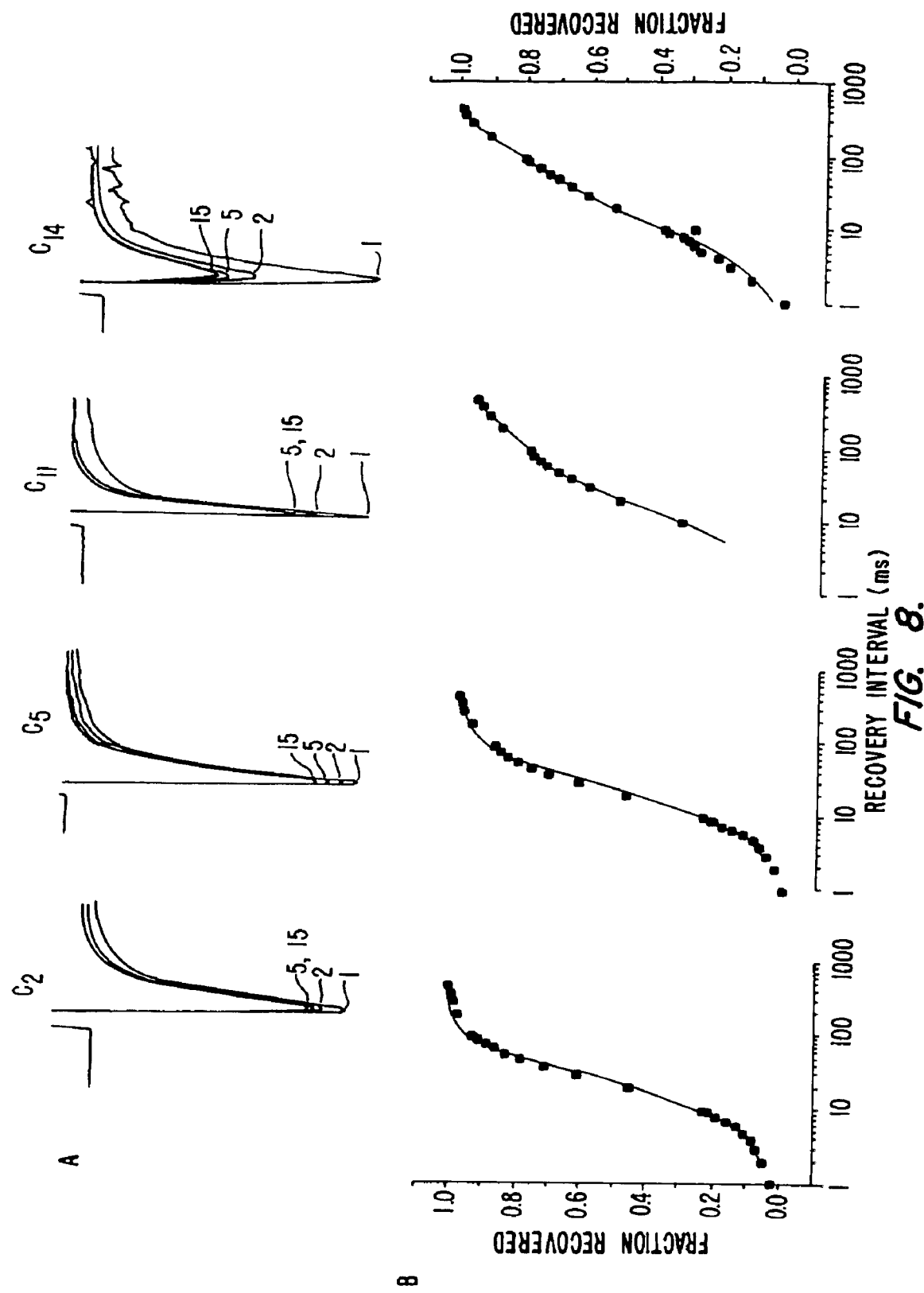
FIG. 8 shows that $C_5^O$, $C_{11}^O$ and $C_{14}^O$ anchoring produces classical local anesthetic actions similar to that observed for $C_2$ (ie., channel block, slowing the rate of recovery from inactivation, and leftward shift in the steady-state inactivation) but with two important exceptions. $C_2$ shows very little use-dependent block as expected from the properties of benzocaine itself
Figure 9:
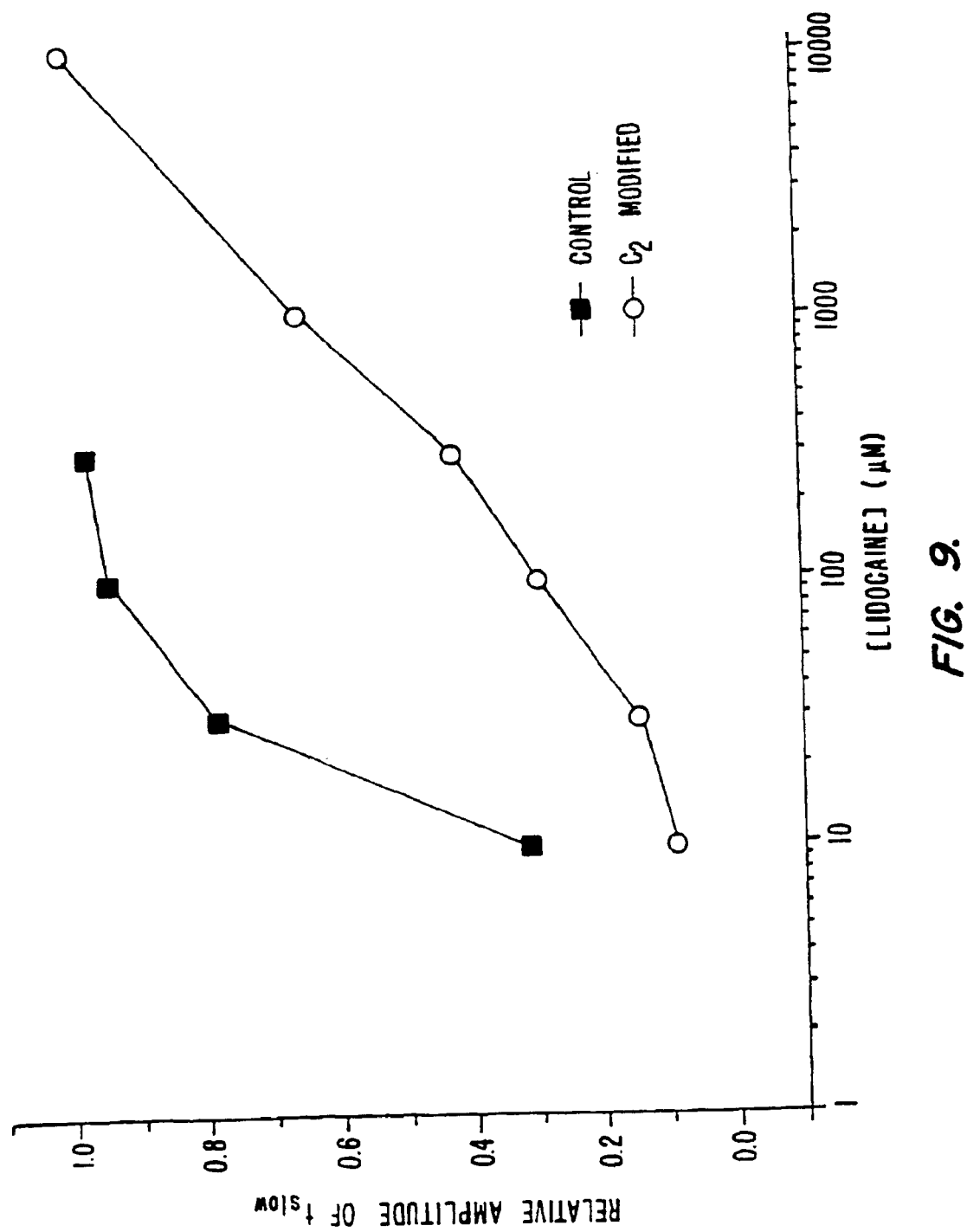
FIG. 9 illustrates studies examining the ability of $C_2$ anchoring to shift the changes in Na$^+$ channel activity produced by the application of lidocaine. $C_2$ shifted the sensitivity of the channels to block by lidocaine by nearly two orders of magnitude.

Preliminary studies have been performed on four prototypes of the drug illustrated in FIG. 3. The chemical structures of these agents are shown in FIG. 2. Studies using these drugs were performed on three distinct types of Na$^+$ channel proteins: skeletal muscle Na$^+$ channel proteins expressed in *Xenopus sp.* oocytes, native heart Na$^+$ channel proteins in isolated rat ventricular myocytes and mutated skeletal muscle Na$^+$ channel proteins (i.e., Y401C) in which the naturally occurring tyrosine at position 401 was replaced with cysteine, the residue naturally found in heart. Native heart Na$^+$ channel proteins and Y401C channel proteins are referred to as "heart-like" Na$^+$ channel proteins.

Results with $C_2$

Application of $C_2$ at concentrations between 100 μM and 1 mM, caused decreases in whole-cell Na$^+$ current, enhanced rates of whole-cell Na$^+$ current decay following channel protein activation, leftward shifts in the steady-state inactivation curve and slowing of recovery from inactivation. Thus, the effects of $C_2$ on Na$^+$ channel proteins are very similar to the effects of nonpolar group 1b agents including benzocaine.

However, the effects of $C_2$ on heart and Y401C Na$^+$ channel proteins (i.e., heart-like Na$^+$ channel proteins) were distinct from their effects on skeletal muscle Na$^+$ channel proteins. Specifically, when the drug is present in the solution bathing the cardiac tissue, Na$^+$ channel protein properties are modified similar to the modification seen when cardiac tissue is in the presence of class 1b antiarrhythmics. However, unlike when the drug is washed out of skeletal tissue, the drug could not be washed out from native Na$^+$ channel proteins and binding of $C_2$ was found to be irreversible. The inability to wash out the effects of $C_2$ was also observed in Y401C channel proteins.

To determine the role of the cysteine in the pore of cardiac Na$^+$ channel proteins, effects of $C_2$ on Na$^+$ channel proteins were examined in the presence of Cd$^{2+}$ and dithiothreitol (DTT). The presence of DTT totally inhibited the irreversable binding of $C_2$ observed following washout of drug from the bath. Thus, it appears that $C_2$ is linked to the Na$^+$ channel protein via a disulfide bond.

Cd$^{2+}$ binds with very high affinity to free sulfhydryls but not disulfide linked sulfhydryls. To determine whether the cysteines are binding to the drug, after washout of the $C_2$ from Na$^+$ channel proteins channel proteins, Cd$^{2+}$ was added. It was found that the Na$^+$ current was no longer blocked by μM amounts of Cd$^{2+}$. Following DTT application, $C_2$ modified channel proteins restore their sensitivity to Cd$^{2+}$ and this restoration occurs simultaneous with the reversal of the local anesthetic effects.

Results using $C_6$, $C_{10}$ and $T_2$

Similar results were obtained with $C_6$, $C_{10}$ and $T_2$. $C_6$ was found to be far more potent than $C_2$. $C_6$ has a longer linking group which allowed a more optimal interaction of the drug with the local anesthetic binding site. $T_2$ demonstrated additional properties not observed with the $C_X$ compounds. Specifically, the amount of Na$^+$ channel proteins blocked by this agent depended on the frequency of stimulation of Na$^+$ channel proteins (i.e., the block of Na$^+$ channel proteins is use-dependent). These studies confirmed that these agents are working in the designed manner, the anchoring group was anchored in the channel pore and delivered the drug to the local anesthetic binding site.

Example 13

Carbohydrate-Based Methanethiosulfonate (MTS) Reagents

The following is an example of how a general class of carbohydrate-based MTS reagents are formed from the well known glycosyl cyanates. The carbohydrates can be non-saccharides. Similar chemistry using glycosyl thiocyanates affords the corresponding thioderivatives.

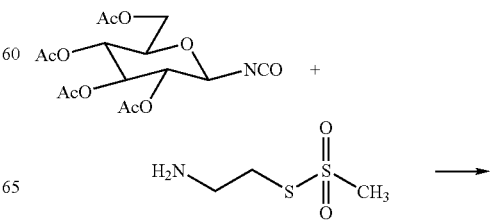

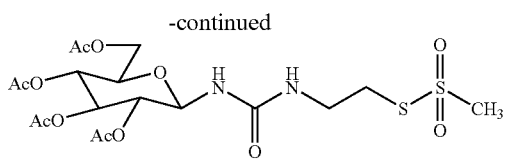

The isocyanate above (1.5 g; 4.02 mmol) was dissolved in 50 mL of dry DMF. Aminoethyl methanethiosulfonate hydrobromide (0.95 g; 4.02 mmol) was added followed by diisopropylamine (0.784 mL; 4.5 mmol). The solvent was evaporated. The residue was applied to a column of silica gel, which was eluted with chloroform:methanol (95:5). The fractions containing product were combined and evaporated to dryness to give the tetraacetate product as a viscous yellow oil of 2.25 g (4.2 mmol).

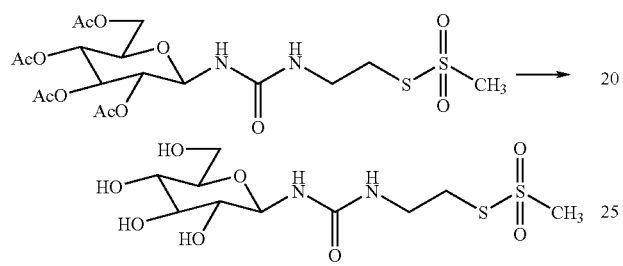

This material was stirred at room temperature overnight in a mixture of 10 mL triethylamine and 90 mL methanol. Then 10 g silica gel was added. The mixture was evaporated to dryness. The residual powder was applied to a column of silica gel and then eluted with methylene chloride:methanol (7:3). The fractions containing product were combined, evaporated to dryness, to give N-glucopyranosyl-N'-2-methanethiosulfonylethyl urea as an off-white solid.

$^1$H NMR (500 MHz, $(CD_3)_2SO$) δ 6.59 (d, J=9.1 Hz, 1H), 6.28 (t, J=5.5 Hz., 1H), 4.89 (d, J=4.7 Hz, 1H), 4.82 (d, J=5.6Hz, 1H), 3.61 (dd, J=5.6 Hz, J=11.3 Hz, 1H), 3.52 (s, 1H), 3,35–3,42 (m, 3H), 3.25 (t, J=6.5 Hz, 2H), 3.15 (ddd, J=4.9 Hz, J=8.8 Hz, J=13.1 Hz, 1H) 3.00–3.07 (m, 2H), 2.92 (dd, J=8.8 Hz, J=14.6 Hz, 1H).

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

| SEQUENCE ID LISTING |
|---|
| GTNGSVEADGLVWESLDLYLSDPENYLLKNGTS (SEQ ID NO:1) |
| TIRGVDTVSRSSLEMSPLAPVNSHERRSKRRKRMSSGTEECGEDRLPKSDSEDGPRA MNHLSLTRGLSRTSMKPRSSRGSIFTFRRRDLGSEADFADDENSTARESESHHTSLLV PWPLRRTSAQGQPSPGTSAPGHALHGKKNSTVDCNGVVSLLGAGDPEATSPGSHLL RPVMLEHPPDTTTPSEEPGGPQMLTSQAPCVDGFEEPGAR (SEQ ID NO:2) |
| WYGNDTWYGNEMWYGNDSWYANDTWNSHASWATNDTFDW (SEQ ID NO:3) |
| EELEKAKAAQALEGGEADGDPAHGKDCNGSLDTSQGEKGAPRQSGSGDSGISDAM (SEQ ID NO:4) |
| MQDAMGYELPWVYFVSLVIF (SEQ ID NO:5) |
| VNDAVGRDWPWIYFVTLIII (SEQ ID NO:6) |
| KHYFCDAWNTFDALIVVGSIVDIAITEVHP (SEQ ID NO:7) |
| KGYFSDPWNVFDFLIVIGSIIDVILSETNP (SEQ ID NO:8) |
| RGTPAGLHAQKKGKFAWFSHSTETH (SEQ ID NO:9) |

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 33 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

```
Gly Thr Asn Gly Ser Val Glu Ala Asp Gly Leu Val Trp Glu Ser Le
1               5                   10                  15

Asp Leu Tyr Leu Ser Asp Pro Glu Asn Tyr Leu Leu Lys Asn Gly Th
                20                  25                  30

Ser
```

(2) INFORMATION FOR SEQ ID NO: 2:

(i) SEQUENCE CHARACTERISTICS:
        (A) LENGTH: 211 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

```
Thr Ile Arg Gly Val Asp Thr Val Ser Arg Ser Ser Leu Glu Met Se
1               5                   10                  15

Pro Leu Ala Pro Val Asn Ser His Glu Arg Arg Ser Lys Arg Arg Ly
                20                  25                  30

Arg Met Ser Ser Gly Thr Glu Glu Cys Gly Glu Asp Arg Leu Pro Ly
                35                  40                  45

Ser Asp Ser Glu Asp Gly Pro Arg Ala Met Asn His Leu Ser Leu Th
50                  55                  60

Arg Gly Leu Ser Arg Thr Ser Met Lys Pro Arg Ser Ser Arg Gly Se
65                  70                  75                  80

Ile Phe Thr Phe Arg Arg Asp Leu Gly Ser Glu Ala Asp Phe Al
                85                  90                  95

Asp Asp Glu Asn Ser Thr Ala Arg Glu Ser Glu Ser His His Thr Se
                100                 105                 110

Leu Leu Val Pro Trp Pro Leu Arg Arg Thr Ser Ala Gln Gly Gln Pr
                115                 120                 125

Ser Pro Gly Thr Ser Ala Pro Gly His Ala Leu His Gly Lys Lys As
                130                 135                 140

Ser Thr Val Asp Cys Asn Gly Val Val Ser Leu Leu Gly Ala Gly As
145                 150                 155                 160

Pro Glu Ala Thr Ser Pro Gly Ser His Leu Leu Arg Pro Val Met Le
                165                 170                 175

Glu His Pro Pro Asp Thr Thr Thr Pro Ser Glu Glu Pro Gly Gly Pr
                180                 185                 190

Gln Met Leu Thr Ser Gln Ala Pro Cys Val Asp Gly Phe Glu Glu Pr
                195                 200                 205

Gly Ala Arg
            210
```

(2) INFORMATION FOR SEQ ID NO: 3:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

```
Trp Tyr Gly Asn Asp Thr Trp Tyr Gly Asn Glu Met Trp Tyr Gly As
1               5                   10                  15
```

```
Asp Ser Trp Tyr Ala Asn Asp Thr Trp Asn Ser His Ala Ser Trp Al
            20                  25                  30

Thr Asn Asp Thr Phe Asp Trp
            35

(2) INFORMATION FOR SEQ ID NO: 4:

(i) SEQUENCE CHARACTERISTICS:
        (A) LENGTH: 55 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Glu Glu Leu Glu Lys Ala Lys Ala Ala Gln Ala Leu Glu Gly Gly Gl
1               5                   10                  15

Ala Asp Gly Asp Pro Ala His Gly Lys Asp Cys Asn Gly Ser Leu As
            20                  25                  30

Thr Ser Gln Gly Glu Lys Gly Ala Pro Arg Gln Ser Gly Ser Gly As
            35                  40                  45

Ser Gly Ile Ser Asp Ala Met
        50              55

(2) INFORMATION FOR SEQ ID NO: 5:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Met Gln Asp Ala Met Gly Tyr Glu Leu Pro Trp Val Tyr Phe Val Se
1               5                   10                  15

Leu Val Ile Phe
            20

(2) INFORMATION FOR SEQ ID NO: 6:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Val Asn Asp Ala Val Gly Arg Asp Trp Pro Trp Ile Tyr Phe Val Th
1               5                   10                  15

Leu Ile Ile Ile
            20

(2) INFORMATION FOR SEQ ID NO: 7:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide
```

(xi) SEQUENCE DESCRIPTION: SEQ ID NO: 7:

Lys His Tyr Phe Cys Asp Ala Trp Asn Thr Phe Asp Ala Leu Ile Va
1               5                   10                  15

Val Gly Ser Ile Val Asp Ile Ala Ile Thr Glu Val His Pro
            20                  25                  30

(2) INFORMATION FOR SEQ ID NO: 8:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Lys Gly Tyr Phe Ser Asp Pro Trp Asn Val Phe Asp Phe Leu Ile Va
1               5                   10                  15

Ile Gly Ser Ile Ile Asp Val Ile Leu Ser Glu Thr Asn Pro
            20                  25                  30

(2) INFORMATION FOR SEQ ID NO: 9:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Arg Gly Thr Pro Ala Gly Leu His Ala Gln Lys Lys Gly Lys Phe Al
1               5                   10                  15

Trp Phe Ser His Ser Thr Glu Thr His
            20                  25

12. The method of claim 1, wherein said compound of formula
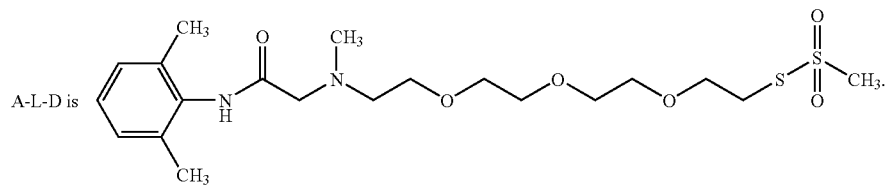

What is claimed is:

1. A method for targeting a drug to a sodium ion channel protein, said method comprising:

contacting said sodium ion channel protein with a compound having the formula

A-L-D wherein:

A is an anchoring moiety that binds selectively, either covalently or electrostatically, to a first binding site on said sodium ion channel protein;

L is a linking group; and

D is a drug that binds to a second binding site on said sodium ion channel protein, wherein said first binding site and said second binding site are distinct; and wherein said compound having the formula A-L-D is selected from the group consisting of

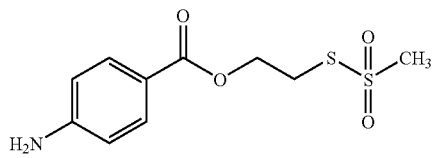

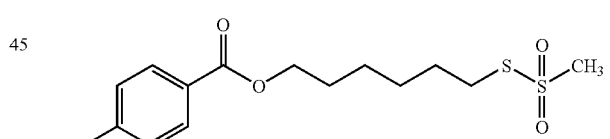

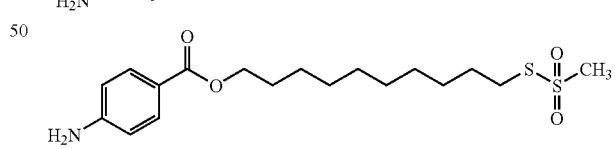

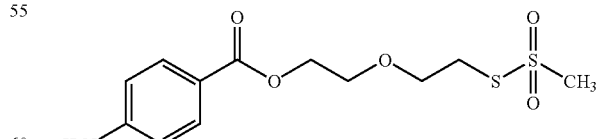

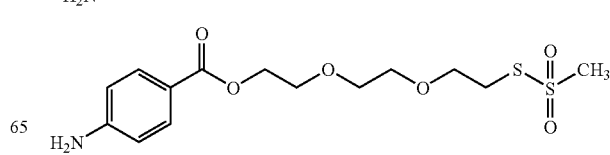

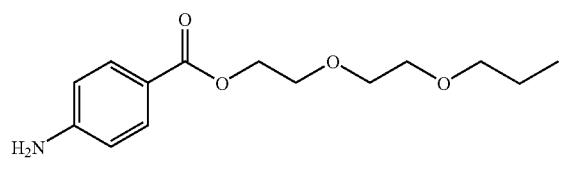
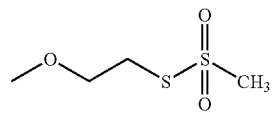
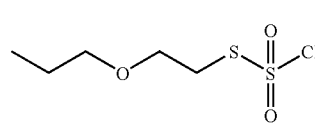
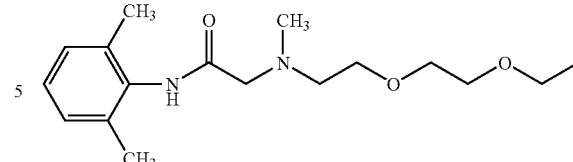
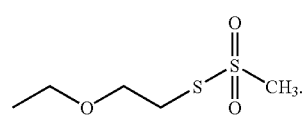
2. The method of claim 1, wherein said compound of formula
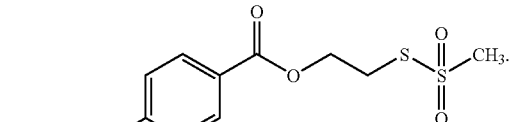
A-L-D is H₂N—
3. The method of claim 1, wherein said compound of formula
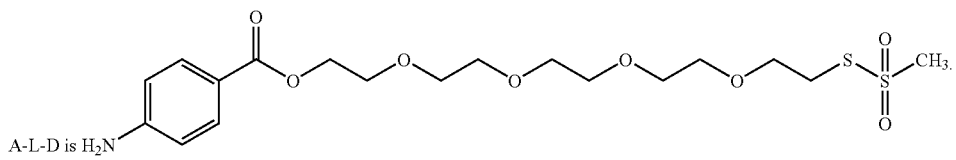
A-L-D is H₂N—
-continued
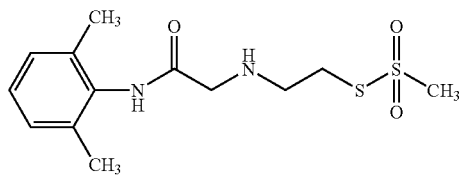
4. The method of claim 1, wherein said compound of formula
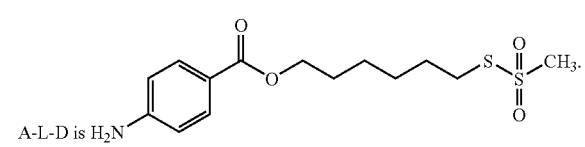
A-L-D is H₂N—
5. The method of claim 1, wherein said compound of formula
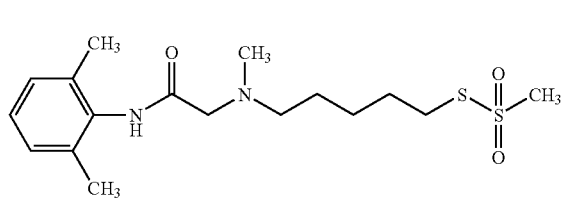
A-L-D is 6. The method of claim 1, wherein said compound of formula

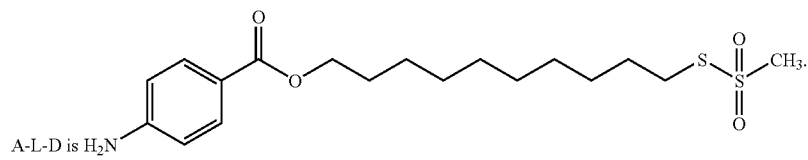

A-L-D is H₂N

7. The method of claim 1, wherein said compound of formula

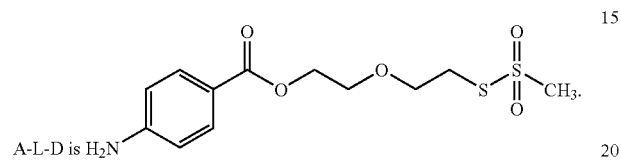

A-L-D is H₂N

8. The method of claim 1, wherein said compound of formula

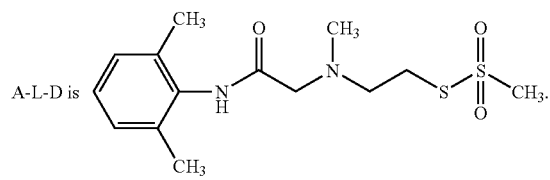

A-L-D is

9. The method of claim 1, wherein said compound of formula

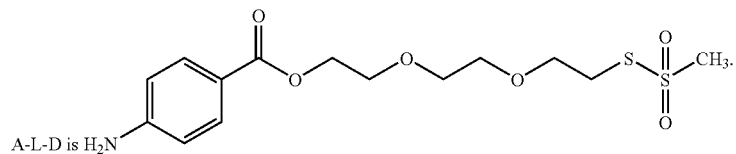

A-L-D is H₂N

10. The method of claim 1, wherein said compound of formula

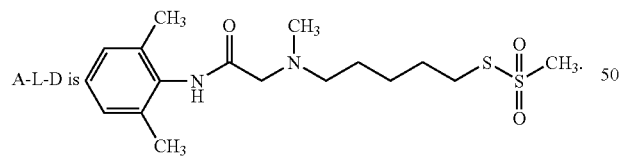

A-L-D is

11. The method of claim 1, wherein said compound of formula

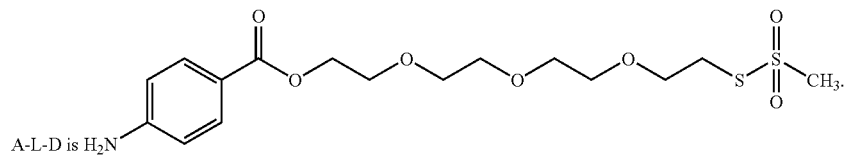

A-L-D is H₂N